(12) United States Patent
Pantages et al.

(10) Patent No.: US 6,261,246 B1
(45) Date of Patent: *Jul. 17, 2001

(54) INTRAVASCULAR IMAGING GUIDEWIRE

(75) Inventors: Anthony J. Pantages, Los Altos; William Martin Belef; Lawrence D. Wasicek, both of San Jose; Donald S. Mamayek, Mountain View; James D. Koger, Santa Cruz; Steven Nelson Roe, San Mateo, all of CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/162,090

(22) Filed: Sep. 28, 1998

Related U.S. Application Data

(63) Continuation-in-part of application No. 08/939,315, filed on Sep. 29, 1997, now Pat. No. 6,078,831.

(51) Int. Cl.[7] .................................. A61B 8/12; A61B 5/00
(52) U.S. Cl. .......................... 600/585; 600/459; 600/463
(58) Field of Search .................................. 600/424, 466, 600/467, 434, 462, 463, 433, 459, 585

(56) References Cited

U.S. PATENT DOCUMENTS

| | | | |
|---|---|---|---|
| 4,794,931 | | 1/1989 | Yock . |
| 4,961,433 | * | 10/1990 | Christian ............................ 600/585 |
| 5,095,911 | * | 3/1992 | Pomeranz ............................ 600/463 |
| 5,115,814 | * | 5/1992 | Griffith et al. . |
| 5,178,159 | * | 1/1993 | Christian ............................ 600/585 |
| 5,240,437 | * | 8/1993 | Christian ............................ 439/668 |
| 5,243,988 | * | 9/1993 | Sieben et al. ....................... 600/463 |
| 5,353,798 | | 10/1994 | Sieben . |
| 5,368,035 | * | 11/1994 | Hamm et al. ....................... 600/463 |
| 5,421,338 | | 6/1995 | Crowley et al. . |
| 5,438,997 | * | 8/1995 | Sieben et al. ....................... 600/463 |
| 5,454,373 | * | 10/1995 | Koger et al. ........................ 600/463 |
| 5,464,016 | * | 11/1995 | Nicholas et al. .................... 600/463 |
| 5,507,301 | | 4/1996 | Wasicek et al. . |
| 5,520,189 | * | 5/1996 | Malinowski et al. ............... 600/466 |
| 5,546,948 | | 8/1996 | Hamm et al. . |
| 5,558,093 | * | 9/1996 | Pomeranz . |
| 5,865,178 | * | 2/1999 | Yock .................................... 600/439 |
| 5,868,685 | * | 2/1999 | Powell et al. ....................... 600/585 |
| 5,868,767 | * | 2/1999 | Farley et al. ........................ 606/159 |
| 5,873,835 | * | 2/1999 | Hastings et al. .................... 600/488 |
| 5,879,305 | * | 3/1999 | Yock et al. .......................... 600/462 |
| 5,902,245 | * | 5/1999 | Yock .................................... 600/463 |
| 5,938,623 | * | 8/1999 | Quiachon et al. .................. 600/585 |
| 5,957,899 | * | 9/1999 | Spears et al. ....................... 604/264 |
| 6,078,831 | * | 9/2000 | Belef et al. . |
| 6,165,127 | * | 12/2000 | Crowley .............................. 600/463 |

\* cited by examiner

*Primary Examiner*—Marvin M. Lateef
*Assistant Examiner*—Shawna J Shaw
(74) *Attorney, Agent, or Firm*—Lyon & Lyon LLP

(57) ABSTRACT

An intravascular imaging guidewire which can accomplish longitudinal translation of an imaging plane allowing imaging of an axial length of a region of interest without moving the guidewire. The imaging guidewire comprises a body in the form of a flexible elongate tubular member. An elongate flexible imaging core is slidably received within the body. The imaging core includes a shaft having an imaging device mounted on its distal end. The body and the imaging core are cooperatively constructed to enable axial translation of the imaging core and imaging device relative to the body. The body has a transparent distal portion extending an axial length over which axially translatable imaging may be performed. The imaging guidewire has a maximum diameter over its entire length sized to be received within a guidewire lumen of an intravascular catheter.

20 Claims, 22 Drawing Sheets

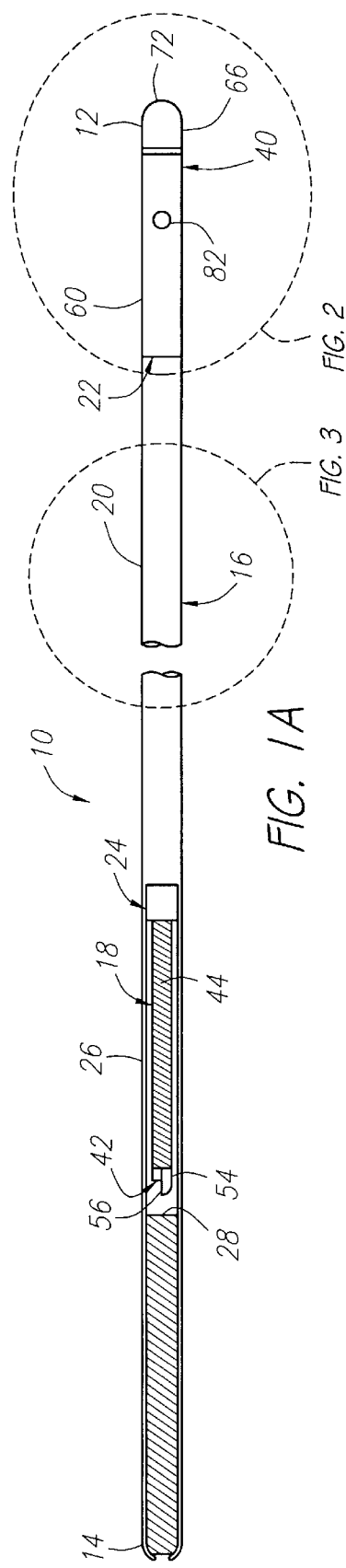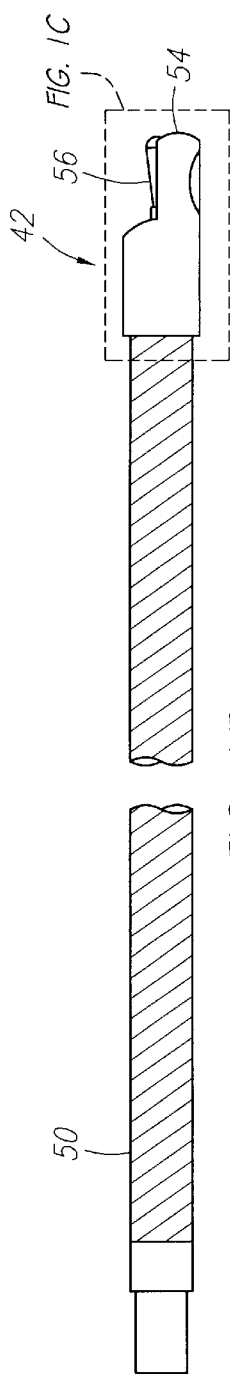

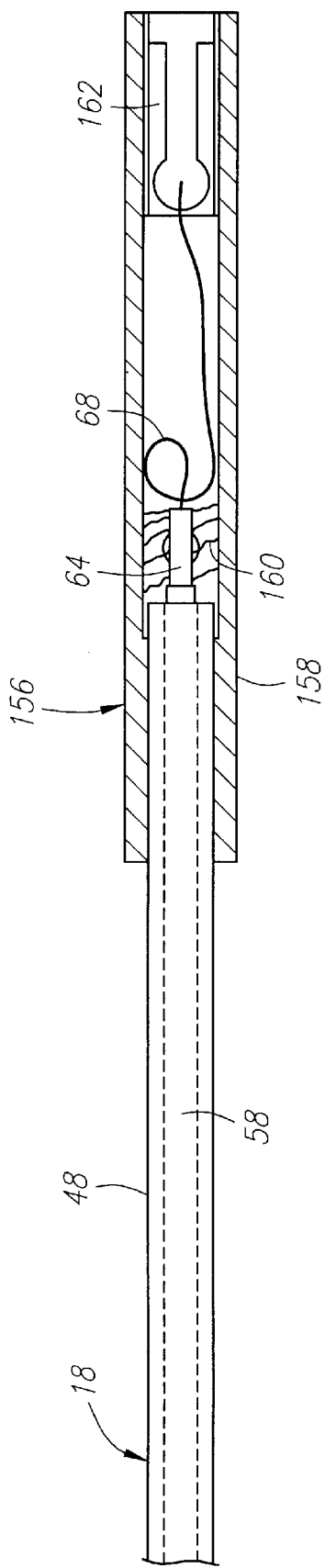
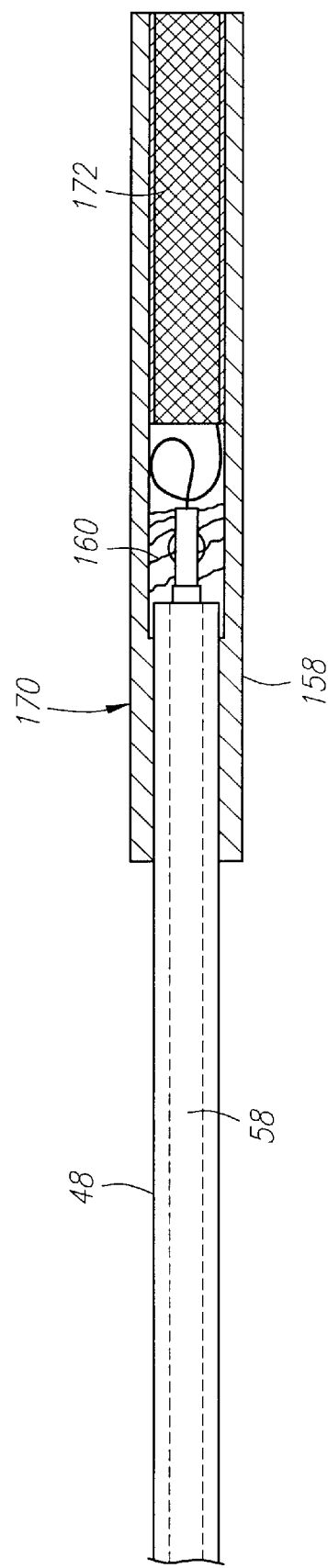
FIG. 2B
FIG. 2C

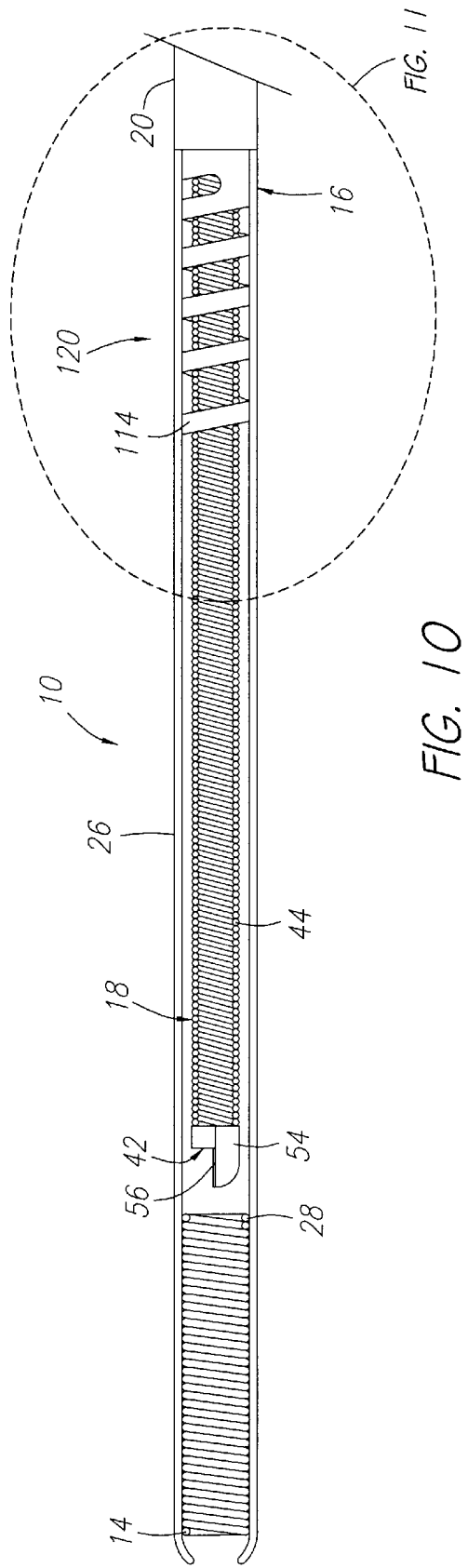
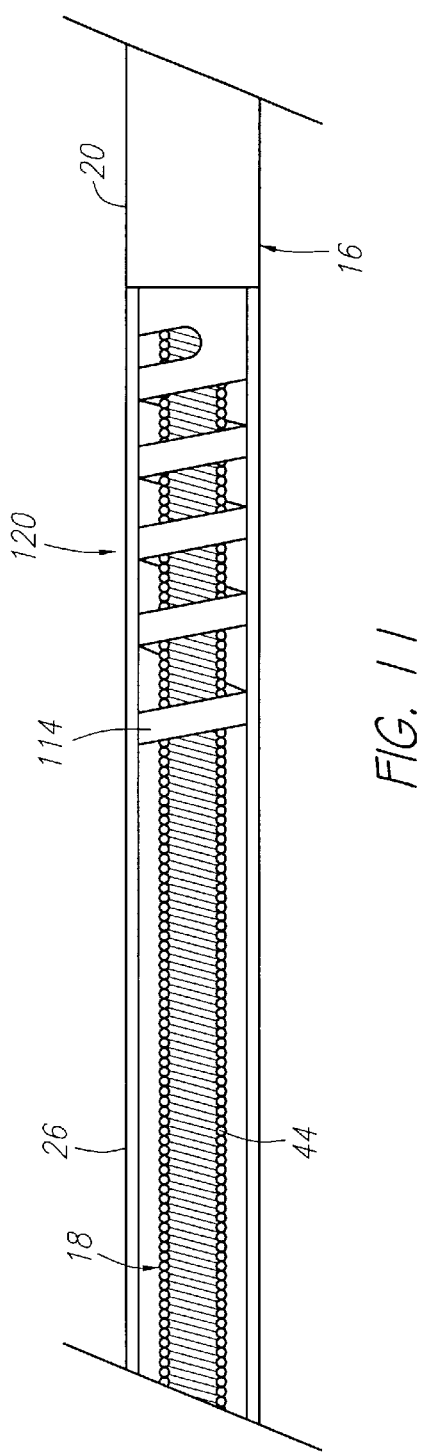
FIG. 10
FIG. 11

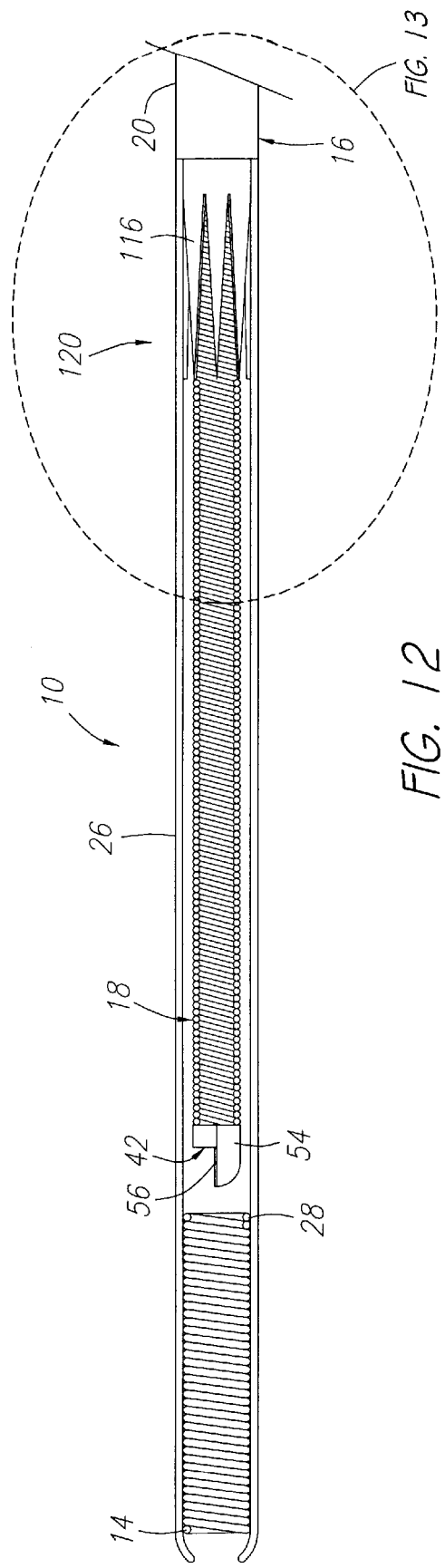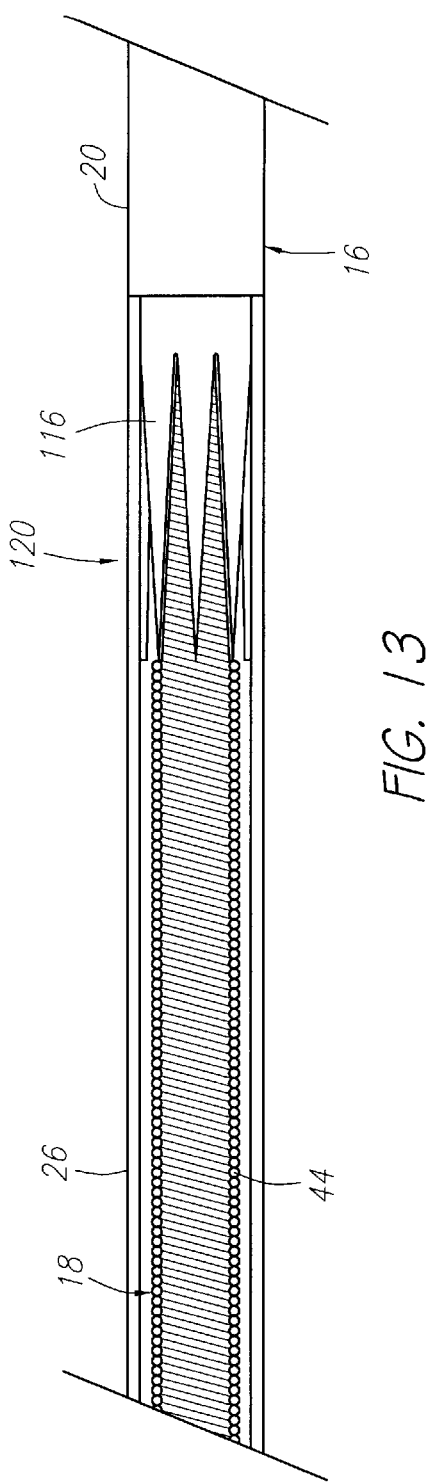

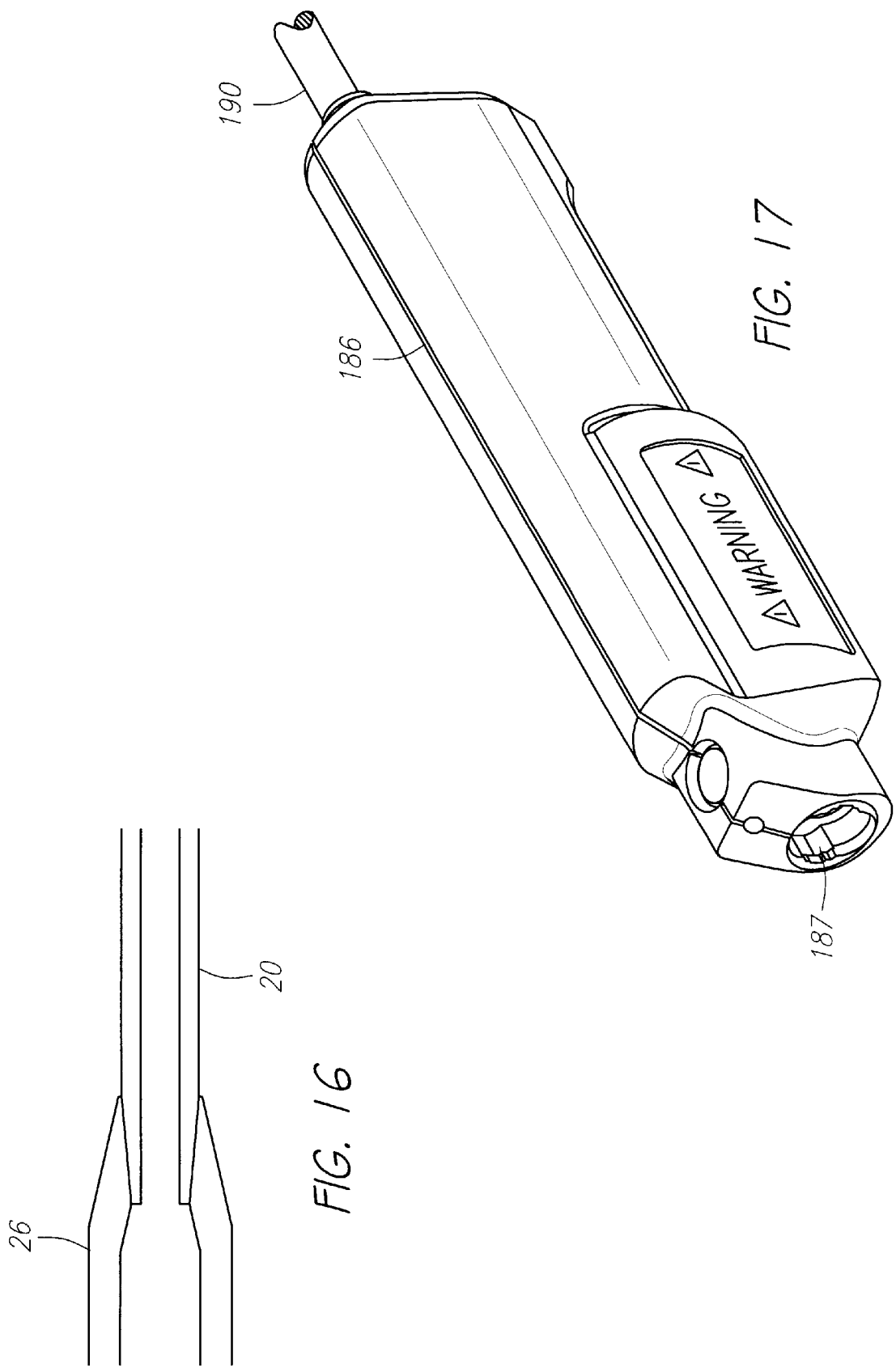

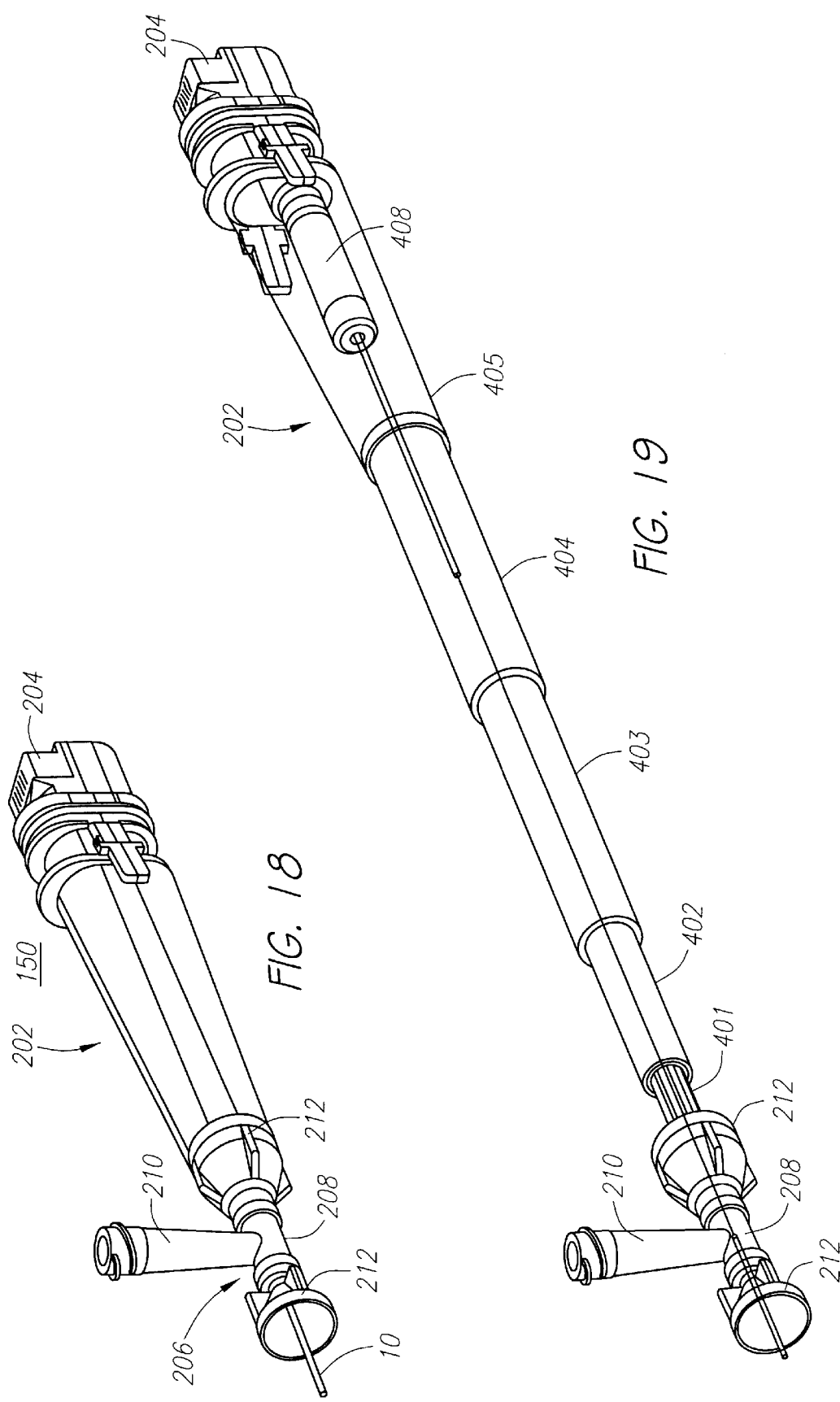

INTRAVASCULAR IMAGING GUIDEWIRE

CROSS-REFERENCE TO RELATED APPLICATION

This application is a continuation-in-part of now U.S. patent application Ser. No. 08/939,315, filed on Sep. 29, 1997, now U.S. Pat. No. 6,078,831 issued Jun. 20, 2000 which is entitled "Intravascular Imaging Guidewire," and is hereby incorporated by reference.

FIELD OF THE INVENTION

The present invention relates to an intravascular imaging guidewire system and to methods for use and manufacture thereof, and more specifically to an imaging guidewire which can be used to receive a therapeutic catheter having a guide lumen to direct the catheter to a desired position within a vessel of a body.

BACKGROUND OF THE INVENTION

Intraluminal, intracavity, intravascular, and intracardiac treatment and diagnosis of medical conditions utilizing minimally invasive procedures is an effective tool in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. The catheter may also be provided with a therapeutic device, such as those used for performing interventional techniques including balloon angioplasty, laser ablation, atherectomy and the like. Catheters also are commonly used for the placement of grafts, stents, stent-grafts, etc., for opening up and/or preventing closure of diseased or damaged vessels.

Catheters having ultrasound imaging and/or therapeutic capabilities are generally known. For example, U.S. Pat. No. 5,313,949, issued to Yock, the disclosure of which is incorporated herein by reference, describes an intravascular ultrasound imaging catheter having an atherectomy cutting device. Generally speaking, there are two predominant techniques used to position the therapeutic catheter at the region of interest within the body. The first technique simply involves directly inserting the catheter into a vessel and advancing the catheter through the branches of the vascular system by pushing and steering the catheter to enter a desired branch as the catheter is moved forward. The use of this technique typically requires that the catheter be equipped with an extremely flexible guidewire at its distal tip that can be aimed in different directions by rotating the catheter or by actuating a steering mechanism.

The second technique utilizes a separate guidewire that is first positioned within the vascular system such that a distal end of the guidewire extends beyond the region of interest. The guidewire is routed into position by inserting it into a vessel and advancing it through the vascular system by pushing and steering the guidewire similar to the method previously described for a catheter. The catheter being inserted includes a guidewire lumen that is sized to receive the guidewire. The guidewire lumen may extend the entire length of the catheter, or alternatively, the guidewire lumen may be a short length lumen disposed at the distal end of the catheter. Once the guidewire is in place, the therapeutic and/or imaging catheter is routed over the guidewire to the region of interest while holding the guidewire fixed in place.

The use of a guidewire provides several advantages. Routing a catheter or guidewire through a circuitous path of the complex network of blood vessels to a region of interest can be a tedious and time consuming task. Placement of the guidewire is made even more difficult with increasing vessel occlusion that may occur in the later stages of vascular disease. In addition, many catheter procedures require the use of several different catheters. For instance, an imaging catheter may be initially inserted to precisely locate and diagnose a diseased region. Then, the imaging catheter may be removed and a therapeutic catheter, such as an balloon angioplasty catheter, may be inserted. Additional therapeutic or imaging catheters may be employed as necessary. Accordingly the successive insertion and removal of each of these catheters, called catheter "exchanges," is required because there is only enough space within the vessels to rout a single catheter at a time. Hence, with the use of a guidewire, the tedious and time-consuming task of routing a device to the region of interest need only be done once. Then, the much easier procedure of routing catheters over the guidewire to the region of interest may be performed as many times as the desired therapy dictates.

In order to locate the site of interest and facilitate proper placement of the guidewire, and further to observe the site during and after treatment, a guidewire may include an imaging device, commonly a rotating ultrasonic imaging transducer or a phased-array ultrasound transducer. Providing the guidewire with imaging capability may eliminate the need for insertion of an imaging catheter or imaging capabilities in the therapeutic catheters. Hence, an imaging guidewire can reduce the number of catheter exchanges that a physician must do during a surgical procedure.

Imaging guidewires have been disclosed generally as, for example, in U.S. Pat. No. 5,095,911, issued to Pomeranz, the disclosure of which is incorporated herein by reference. The imaging guidewire disclosed in Pomeranz includes an elongate, flexible body. A housing enclosing a rotating transducer is secured to the distal end of the body. A drive shaft extends through a lumen of the body and is coupled to the transducer. In order to image a different region of interest, the entire guidewire is moved back and forth to position the housing and transducer adjacent the region.

However, once the physician has carefully placed the imaging guidewire, it is preferable to maintain the guidewire in a fixed position so as not to lose the correct placement of the guidewire. At the same time, it is often desirable to obtain images along an axial length of diseased area. This currently requires axial translation of the imaging device by axially translating the entire guidewire. The problem with advancing and pulling back the imaging guidewire is that the correct placement of the guidewire may be lost and the physician must then spend more time repositioning the guidewire.

Furthermore, there are significant technical obstacles in producing an imaging guidewire having a sufficiently small diameter to fit within a guidewire lumen of a catheter while at the same time exhibiting the necessary mechanical and electrical characteristics required for placement in the vascular system and generation of high quality images. For instance, on typical catheters sized to be inserted in the smaller coronary vessels, the guidewire lumen preferably is sized to receive a guidewire having a maximum diameter of 0.014". However, where larger vessels, such as peripheral vessels, are to be imaged, the guidewire lumen may be sized to receive a guidewire having, for example, a maximum diameter of 0.035". In addition, the guidewire preferably has sufficient flexibility to traverse a tortous path through the vascular system, and also has sufficient column strength, or pushability, to transmit a pushing force from a remote proximal end of the guidewire, along a winding path, to the distal end thereof.

Moreover, if a rotating transducer is utilized, the drive shaft extending to the transducer should have stable torsional transmittance in order to achieve high quality images. Hence, the drive shaft should not only be flexible, but also should be torsionally stiff to limit angular deflection and nonuniform angular velocity that can cause image distortion. The drive shaft also should be mechanically and electrically connectable to a drive unit and to transducer signal processing electronics. The connection preferably is easily disconnectable so that a guidewire lumen of a catheter may be threaded over the proximal end of the guidewire. This requirement also limits the size of the connector on the drive shaft because the connector must also fit through the guidewire lumen. The drive shaft and connector also should provide a high quality transmission of imaging signals between the imaging device and the signal processing equipment.

Therefore, a need exists for an improved imaging guidewire that overcomes the aforementioned obstacles and deficiencies of currently available guidewires.

SUMMARY OF THE INVENTION

The present invention provides an intravascular imaging guidewire, and methods of use and manufacture, which can accomplish longitudinal translation of an imaging plane allowing imaging of an axial length of a region of interest without moving the guidewire thereby maintaining proper positioning of the guidewire to effectively facilitate the introduction of catheters over the guidewire to the proper position. The imaging guidewire disconnectably mates to a drive unit. The drive unit acts as an interface and connects to signal processing equipment which comprises electronics to transmit, receive and process imaging signals to and from the imaging guidewire.

Accordingly, the imaging guidewire of the present invention comprises a body in the form of a flexible, elongate tubular member. An elongate, flexible imaging core is preferably slidably and rotatably received within the body. Rotation and longitudinal translation of the imaging core is preferred in order to provide a 360° scan, but it is contemplated in the present invention that the imaging core may also be non-rotating, for example an imaging core having a phased-array ultrasound transducer.

The imaging core includes a rotatable drive shaft having an imaging device mounted on its distal end. The imaging device produces an imaging signal that can be processed by the signal processing equipment to create an image of the feature at which the imaging device is directed. An electrical cable runs through the center of the drive shaft extending from the imaging device at the distal end to a connector attached to the proximal end of the drive shaft. The connector detachably connects the driveshaft to a drive unit and electrically connects the electrical cable to the drive unit and in turn to the signal processing equipment. At least a distal portion of the body through which the imaging device images preferably is substantially transparent to imaging signals received by the imaging device. The transparent portion of the body preferably extends for at least an axial length over which imaging typically will be desirable.

The body and the imaging core are cooperatively constructed to enable axial translation of the imaging core and imaging device relative to the body. This allows imaging along an axial length of a diseased region in the patient's body without moving the guidewire body.

As described above, the imaging guidewire connects to a drive unit. The principle function of the drive unit is to provide an interface between the imaging guidewire and the signal processing equipment. The drive unit, therefore, transmits the imaging signal between the imaging guidewire and the signal processing equipment. In a further aspect of the present invention, in the preferred embodiment comprising a rotating transducer, the drive unit has a motor to rotate the imaging core for providing a 360° scan. In an alternative embodiment, the motor for rotating the imaging core may be part of the signal processing equipment. In this case, the drive unit simply has a drive shaft that is detachably coupled to the motor of the signal processing equipment.

In a further aspect, a coupling device, such as a slip ring assembly or an innovative inductive or capacitive coupling in accordance with one aspect of the present invention, may be provided in the drive unit or within an associated adapter to transmit the imaging signals from the rotating electrical cable within the guidewire drive shaft to the non-rotating electronics within the drive unit. In an alternative embodiment having the motor in the signal processing equipment, the coupling device may be contained in the signal processing equipment.

In a particularly innovative alternative embodiment, the connector on the proximal end of the drive shaft is adapted to provide only a mechanical connection to the mating connector on the drive unit or adapter. For a rotating imaging core, the mechanical connection transmits torque from the drive unit or adapter to the imaging core. In this embodiment, the imaging signal is transmitted from the imaging guidewire connector to the drive unit or adapter via a capacitive coupling or inductive coupling. One element of the coupling is disposed on the draft shaft and rotates with the drive shaft. The other element of the coupling is mounted in the drive unit or adapter and may be rotating or non-rotating.

As is suggested above, in an additional aspect of the present invention, an adapter may be utilized which performs the function of providing an interface between the imaging guidewire and the drive unit. The adapter comprises a connector which mates to the imaging guidewire connector. The imaging guidewire connector plugs into the adapter which in turn mounts into the drive unit. In the preferred embodiment, the adapter makes both the mechanical and the electrical connections to the imaging guidewire. Furthermore, the coupling device of the drive unit may be contained in the adapter instead. In this way, the coupling device transmits the imaging signals from the rotating electrical cable within the guidewire drive shaft to non-rotating electronics within the adapter. Mounting the adapter into the drive unit electrically connects the adapter to the drive unit, for example via mating electrical connectors.

In the preferred method of using the imaging guidewire of present invention, the imaging guidewire is first inserted percutaneously into a vessel of the vascular system, usually at a site remote from the site of interest within the body. The imaging guidewire is routed to the region of interest by advancing it through the branches of the vascular system by pushing and steering the guidewire as the guidewire is fed into the vessel. The imaging device may be activated during this process to aid in routing the guidewire and locating a diseased region of the body. The imaging guidewire is positioned such that the distal end extends beyond the diseased region with the transparent portion of the body approximately centered at the region of interest.

Alternatively, a standard guidewire may first be inserted and routed to the region of interest. Then, a catheter having a full-length guidewire lumen is fully inserted over the standard guidewire. The standard guidewire is then removed and the imaging guidewire is inserted through the guidewire lumen to the desired position.

At this point, in order to image the length of the diseased region, the imaging device may be axially translated forward and back relative to the body which is preferably fixed in place.

Once the medical condition has been diagnosed and a treatment is chosen, a therapeutic catheter having a guidewire lumen, or a series of therapeutic catheters, may be routed over the guidewire to the diseased region to perform the desired treatment. To facilitate the catheter exchanges over the guidewire, the imaging guidewire is disconnected from the drive unit by simply disconnecting the guidewire connector from the drive unit. Once the exchange is complete, the imaging guidewire is reconnected to the drive unit. The imaging device on the guidewire may further be used to monitor the treatment while it is being performed and/or to observe the treated area after the treatment is completed. Alternatively, if the imaging device cannot image through the therapeutic catheter, the catheter may be pulled back to expose the imaging device.

Accordingly, it is an object of the present invention to provide an improved imaging guidewire and method of using the same.

A further object of the present invention is to provide an improved imaging guidewire that can image along an axial length of a region of interest while maintaining a fixed guidewire position.

BRIEF DESCRIPTION OF THE DRAWINGS

FIG. 1(A) is a partial cross-sectional view of an imaging guidewire in accordance with the present invention.

FIG. 1(B) is a partial cross-sectional view of an imaging core in accordance with the present invention.

FIG. 1(C) is a cross-sectional view of an imaging device that may be coupled to an imaging core in accordance with the present invention.

FIG. 2(B) is a partial view of an imaging core having another imaging guidewire connector.

FIG. 2(C) is a partial view of an imaging core having still another imaging guidewire connector.

FIG. 10 is a partial cross-sectional view of yet another alternative imaging guidewire in accordance with the present invention.

FIG. 11 is an expanded cross-sectional view of the region as designated in FIG. 10.

FIG. 12 is a partial cross-sectional view of still another alternative imaging guidewire in accordance with the present invention.

FIG. 13 is an expanded cross-sectional view of the region as designated in FIG. 12.

FIG. 16 is a cross-sectional view of still another embodiment of the imaging guidewire in accordance with the present invention.

FIG. 17 is an illustration of a motor drive unit (MDU) that may be used with an imaging guidewire in accordance with the present invention.

FIG. 18 is a perspective view of a telescoping adapter in accordance with the present invention.

FIG. 19 is a perspective view of the telescoping adapter shown in FIG. 18 in an extended position.

DETAILED DESCRIPTION OF THE INVENTION

Figure 1:
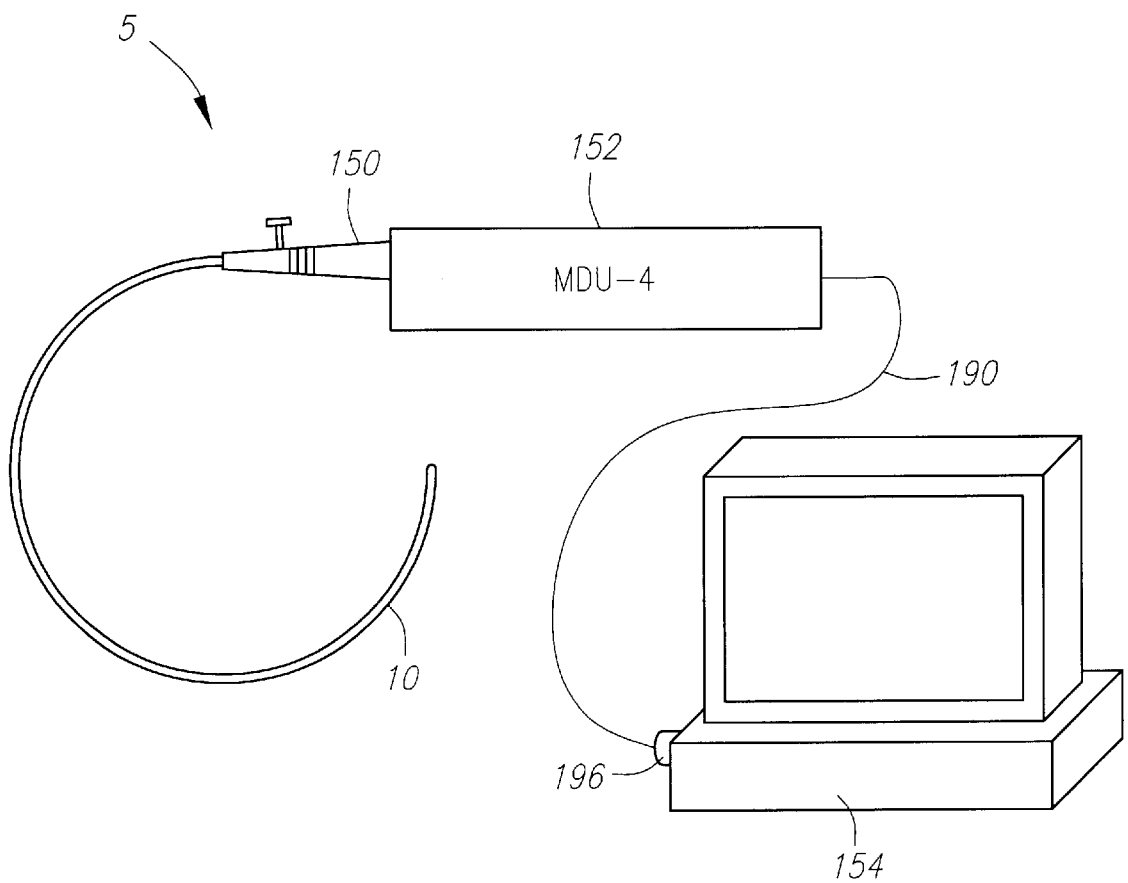
FIG. 1 is a schematic diagram of an intravascular imaging guidewire system in accordance with the present invention.

Turning now to the drawings, FIG. 1 is a schematic diagram of an intravascular imaging guidewire system 5 in accordance with a preferred embodiment of the present invention. The system 5 comprises a imaging guidewire 10 which is adapted to be inserted into a lumen of the body and preferably within the vascular system of the body. The imaging guidewire 10 detachably connects to an adapter 150. The adapter 150 plugs into a motor drive unit 152. The drive unit 152 is connected to signal processing equipment 154. Below, various exemplary embodiments of each of these subsystems of the imaging guidewire system 5 will be described with reference to the drawings. While the exemplary embodiments of the imaging guidewire system 5 that are described herein include both an adapter 150 and a separate motor drive unit 152, it is to be understood that the functionality and essential structure of the adapter 150 may be integrated into the motor drive unit 152, thereby eliminating the adapter 150 from the guidewire system 5. In that case, the imaging guidewire 10 would detachably connect directly to the motor drive unit 152.

Referring to FIGS. 1(A)–3, an imaging guidewire 10 is depicted according to one embodiment of the present invention. In general, the guidewire 10 preferably is flexible enough to traverse a circuitous path through the vascular system, and yet has sufficient pushability to transmit a pushing force from a remote proximal end 12 of the guidewire 10, along a winding path, to a distal end 14 of the guidewire 10. The imaging guidewire 10 also preferably has sufficient torsional stiffness to reliably transmit rotational force applied at the proximal end 12 to the distal end 14 so that the guidewire 10 can be steered through the branches of vessels of the vascular system. However, those skilled in the art will recognize that the required functional characteristics of the guidewire 10 will vary from application to application. Thus, while the above-described functional characteristics are presently preferred, such characteristics need not be inherent in all embodiments of a guidewire in accordance with the present invention.

The imaging guidewire 10 comprises a guidewire body 16 in the form of a flexible, elongate tubular member that slidably and rotatably houses an elongate, flexible, rotating imaging core 18. The imaging guidewire 10 has a substantially uniform diameter and no component along the entire length of the guidewire 10 exceeds a predetermined diameter. This maximum diameter is preferably 0.035" because guidewire lumens of typical catheters sized to be inserted into peripheral vessels are sized to receive a guidewire having a maximum diameter of 0.035". The overall length of the guidewire 10 varies depending on the intended application but may preferably range between 40 cm and 300 cm.

The guidewire body 16 includes a main body 20 having a proximal end 22 and a distal end 24. The main body 20 extends from a connector 40 of the imaging core 18 at its proximal end 22 to a predetermined distance, preferably approximately 15 to 20 cm, from the distal end 14 of the guidewire 10 at its distal end 24. The main body 20 is preferably formed of NITINOL hypotube because it exhibits strength and flexibility properties desired in a guidewire body. NITINOL is also preferred because it minimizes kinking, has a convenient transition temperature below which it transitions to a "soft" state, and is a memory metal such that it returns to its original shape after being bent under specific temperature conditions. Those skilled in the art would appreciate that other materials including other superelastic materials, other metal alloys, and plastics may also be used. It is to be understood that where NITINOL is specified as the preferred material, other materials, including alternative superelastic materials, metal alloy, composite materials and plastics may also be utilized. For example, it is contemplated that the main body 20 may be formed of braided polyimide, polyethylene, peek braids, or stainless steel. The NITINOL main body 20 preferably has an outer diameter of approximately 0.035".

An imaging portion 26 of the guidewire body 16 is connected to the distal end 24 of the main body 20 and extends to the distal end 14 of the guidewire body 16. The imaging portion 26 is substantially transparent to imaging signals transmitted and/or received by an imaging device 42 of the imaging core 18. In a preferred form, the imaging portion 26 is formed of a polyethylene plastic tube that is interference fit onto the distal end 24 of the main body 20. Alternatively, any other suitable attachment method may be employed such as adhesives, mechanical connectors, etc. In further alternative embodiments, the imaging portion 26 may be coextruded, multi-layer, or composite. As examples, the imaging portion 26 may be polyester, nylon, polymeric strands, or metal braid with a long pitch.

A floppy tip 28 preferably is placed inside, and at the distal end of, the imaging portion 26. The floppy tip 28 is designed to prevent trauma to the aorta and to assist in maneuvering the imaging guidewire 10 through a patient's vessels. In some embodiments, the floppy tip 28 can be aimed in different directions by rotating the catheter or by actuating a steering mechanism (not shown). The floppy tip 28 is preferably formed from a flexible coil spring that is radiopaque so as to be visible under fluoroscopy. The floppy tip 28 is held in place by thermally forming the imaging portion 26 over the floppy tip 28 or alternatively using any other suitable attachment technique such as adhesives, press fit, connectors, fasteners, etc. Alternatively, the floppy tip 28 may be a coil in a polymer, a tungsten core with a polyethylene cover, or a standard guidewire tip such as those produce by Lake Region, Inc.

In an alternative form, the guidewire 10 is constructed without the floppy tip 28 leaving the distal extremity greater flexibility. In this case, a radiopaque maker band is placed at the distal end of the imaging portion 26.

Figure 2:
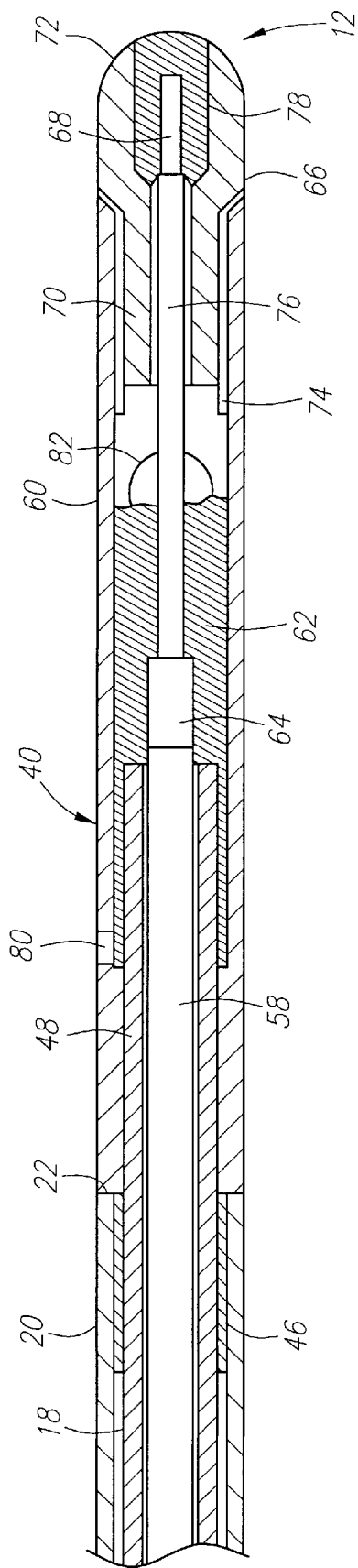
FIG. 2 is an expanded cross-sectional view of the proximal region of the imaging guidewire as designated in FIG. 1(A).

The imaging core 18 principally comprises a tubular drive shaft 44 having an imaging device 46 attached to a distal end of the drive shaft 44 and the connector 40 attached to a proximal end of the drive shaft 44. The drive shaft 44 may be composed of a single tubular member (not shown), or preferably, it may be several elements attached together as shown in FIGS. 1(A)–2. The drive shaft 44 is preferably formed of a NITINOL tube having an outer diameter of approximately 0.022", and in some currently preferred embodiments, such as that illustrated in FIG. 2, may include a telescoping section 48.

Figure 3:
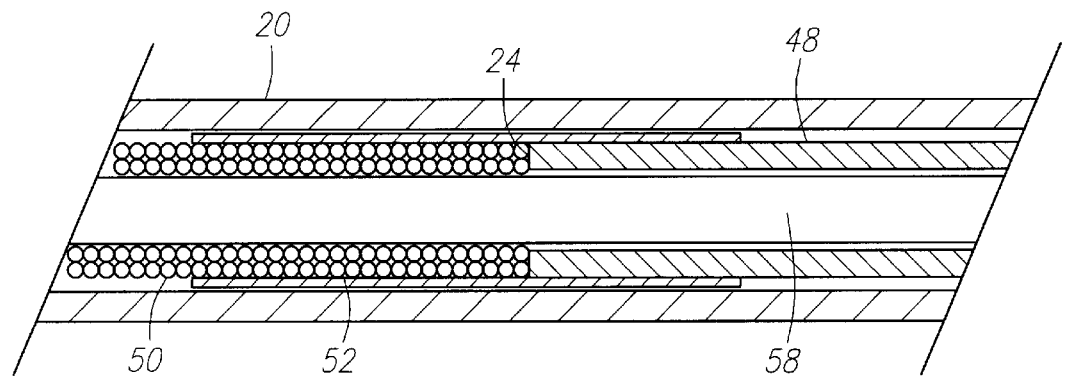
FIG. 3 is an expanded cross-sectional view of the region as designated in FIG. 1.

The telescope portion 48 acts as a telescoping extension of the drive shaft 44 and preferably is of a length approximately the same as the desired length of axial translation of the imaging device 42, preferably around 15 cm. The telescope portion 48 is connected to the connector 40 at its proximal end (shown in FIG. 2) and extends distally to a distal end that is attached to a proximal end of a drive cable 50 (shown in FIG. 3). The drive cable 50 is preferably of a counter-wound, multi-filar coil construction as best shown in FIG. 3 and described in U.S. Pat. No. 4,951,677, to Crowley et al., the disclosure of which is incorporated herein by reference. The telescope portion 48 is attached to the drive cable 50 using a coupler 52 (shown in FIG. 3). One end of the coupler 52 is attached to the telescope portion 48 using an interference fit. The interference fit may be accomplished by cooling the NITINOL telescope portion 48 below its transition temperature such that it becomes soft. The coupler 52 is then slid onto the telescope portion 48 and when warmed above the transition temperature, a secure interference fit results. The other end of the coupler 52 is attached to the drive cable 50, preferably using an adhesive, although any suitable attachment means is contemplated. The coupler 52 also functions as a stop which interferes with a stop collar 46 (shown in FIG. 2) attached to the inside of the proximal end 22 of the main body 20 which limits the proximal axial translation of the imaging core 18 relative to the guidewire body 16. The stop collar 46 may also be interference fit into the NITINOL main body 20 using the same method just described for attaching the coupler 52 to the telescope portion 48.

The imaging device 42 is attached to the distal end of the drive cable 50, as is shown in FIGS. 1(A)–1(C). The imaging device 42 may be any type device that creates a high quality imaging signal of the body tissue to be imaged, but is preferably an ultrasound imaging device. The imaging device 42 includes a housing 54 into which an ultrasound transducer 56 is mounted. The design, construction and use of ultrasound imaging devices is generally known in the art and therefore a detailed description is not included herein. The ultrasound transducer 56 is oriented to image in a radially outward direction and when rotated with the drive shaft 44 creates a 360° radial scan of the surrounding tissue. Alternatively, the ultrasound transducer 56 may be oriented such that it images in a forward looking or backward looking direction or any angle in between.

To transmit the imaging signal from the imaging device 56 to the connector 40, a coaxial cable 58 is attached to the imaging device 42 which runs down the center of the drive shaft 44 where the other end of the coaxial cable 58 is attached to the connector 40. The connector 40 detachably connects to the adapter 150.

Turning again to FIG. 2, an innovative connector 40 will be described in detail. Overall, the connector 40 is cylindrically shaped and has a maximum diameter not exceeding the diameter of the remainder of the guidewire 10, which is preferably 0.035" in diameter. The distal end of the connector 40 is composed of a conductive ring 60 which is attached to the proximal end of the telescope portion 48 by an interference fit as shown, or by any other suitable attachment method. The conductive ring 60 is filled with conductive epoxy 62 through a fill hole 80 to cover the outer lead 64 of the coaxial cable 58 thereby electrically connecting the conductive ring 60 to the outer lead 64 and completing one pole of the imaging device 42 circuit. The conductive ring 60 may have a second hole 82 to observe the amount of epoxy being inserted to ensure that it does not overfill and electrically connect to a second conductor 66. The second conductor 66 has a stepped tubular section 70 and a ball-shaped end 72. The stepped tubular section 70 is covered with an insulator 74 such as a piece of shrink tubing. The stepped tubular section 70 covered with the insulator 74 inserts into the conductive ring 60 and is bonded in place using an adhesive such as cyanoacrylate. The insulator 74 electrically insulates the conductive ring 60 from the second conductor 66. The inner lead 68 and insulation 76 of the coaxial cable 58 extend through the first conductive epoxy 62 and through the stepped tubular section 70. The inner lead 68 further extends into a cavity in the ball-shaped end 72. The cavity in the ball-shaped end 72 is filled with a second conductive epoxy 78 to conductively connect the second conductor 66 to the inner lead 68 completing the other pole of the imaging device 42 circuit.

Hence, connector 40 provides a detachable electrical and mechanical attachment to the adapter 150 and in turn to the drive unit 152 and the signal processing equipment 154. The detachability feature allows the guidewire 10 to be quickly and easily disconnected so that catheters may be inserted over the guidewire 10 and, then just as easily, the guidewire 10 can be reconnected.

Figure 2A:
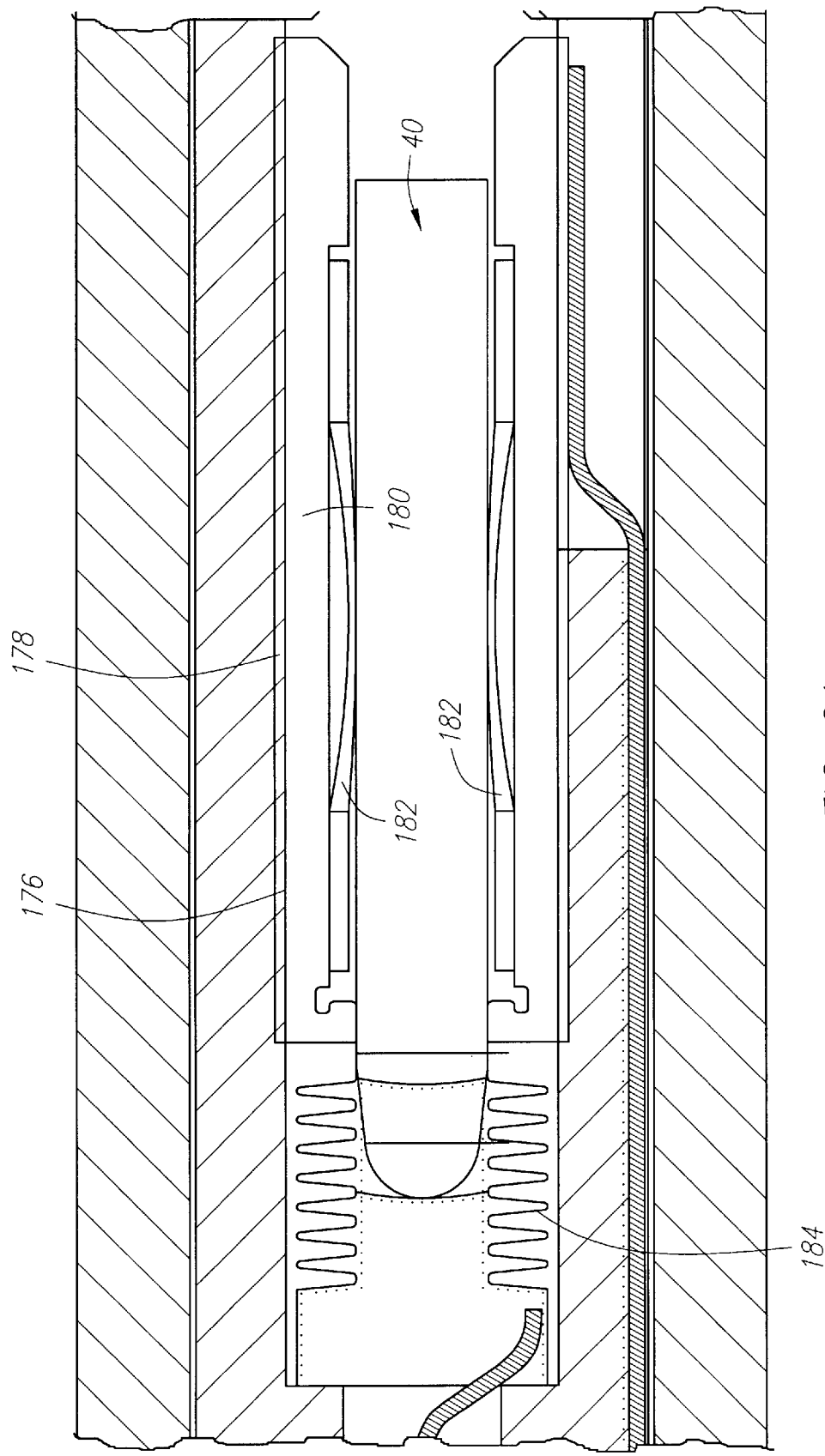
FIG. 2(A) is a cross-sectional view of a mating connector that may be used with the imaging guidewire connector shown in FIG. 2.

FIG. 2(A) depicts an exemplary mating connector 176 with the connector 40 inserted into it. The mating connector 176 is installed in the adapter 150 as will be described in detail below. The mating connector 176 includes a first contact 178 which is preferably a cylindrical multi-contact socket connector. The first contact 178 comprises a cylindrical body 180 which houses at least one, but preferable a plurality of, spring-loaded bands 182. The spring-loaded bands 182 and body 180 are formed of an electrically conductive material such as copper alloy. The first contact 178 receives the conductive ring 60 of the guidewire connector 10 and preferably provides sufficient contact friction to drive the rotation of the imaging core 18. If needed a locking mechanism, such as a key and slot, may be provided on the connector 40 and the mating connector 176 to prevent slippage when the connectors 40 and 176 are being rotated. A second contact 184 forms the proximal portion of the connector 176 and is preferably a small bellows type connector. When the guidewire connector 40 is connected to the mating connector 176, the conductive ring 60 contacts the first contact 178, and the ball shaped end 72 contacts the second contact 184, thereby electrically connecting the imaging guidewire 10 to the adapter 150 and drive unit 152.

FIG. 2(B) shows a partial view of an imaging core 18 having another exemplary imaging guidewire connector 156. The guidewire body 16 is not shown in FIG. 2(A). It should be appreciated that the structure shown in FIG. 2(A), as well as any of the other connectors describe herein, are contemplated to be used on any of the disclosed guidewires with at most minor modifications. The connector 156 is attached to the proximal end of the drive shaft 44 of the imaging core 18. Generally, the connector 156 is similar to a typical shield connector. The connector 156 is cyclindrically shaped and has a maximum diameter not exceeding the diameter of the guidewire, which is preferably 0.035'. The connector 156 comprises a cylindrical conductive shell 158 which is attached to the proximal end of the drive shaft 44. A portion of the shell 158 is filled with conductive epoxy 160 thereby electrically connecting the shell 158 to the outer lead 64 of the coaxial cable 58. A flex circuit 162 printed on polyimide, for example, is rolled into a tube and inserted into the proximal end of the shell 158. The flex circuit 162 has a conductive trace printed on the interior surface of the tubular flex circuit 162 and the polyimide exterior serves as an insulator between the conductive trace and the shell 158. The flex circuit 162 may be bonded in place using any known suitable means such as epoxy adhesive.

Still another exemplary connector 170 is shown in FIG. 2(C) and is identical to the mating connector 156 except that the flex circuit 162 is replaced by a braided contact 172. The braided contact 172 may be formed using a piece of polyimide tubing with stainless steel or copper braiding embedded in the tubing, with the braid slightly exposed in the inner diameter.

Figure 2D:
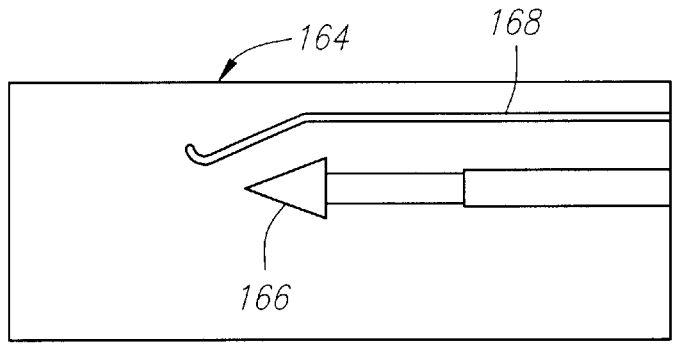
FIG. 2(D) is a schematic view of a connector that may mate with the connectors shown in FIGS. 2(B) and 2(C).

An exemplary mating connector 164 which connects to the connectors 156 and 170 is shown in FIG. 2(D). The mating connector 164 is installed in the adapter 150 as described below. The mating connector 164 includes a cone tipped spring contact 166 which is adapted to be inserted into the opening of the connectors 156 and 170 described above and contacts the flex circuit 162 or braided contact 172, respectively. A flat wire slip contact 168 is disposed radially outward from the spring contact 166 so that it contacts the outside of the shell 158 of the connectors 156 and 170 when the connectors are mated. The slip contact 168 may alternatively be replaced by a cylindrical multi-contact socket connector (not shown).

Figure 2E:
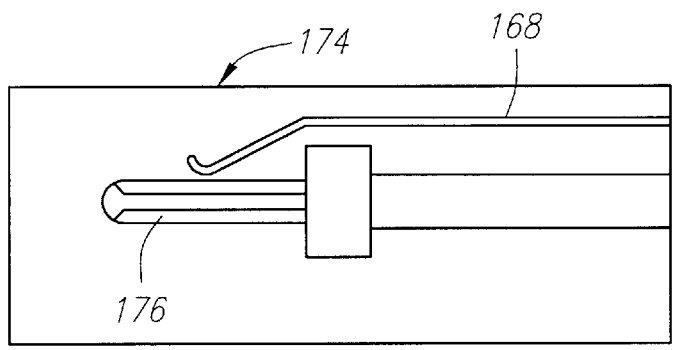
FIG. 2(E) is a schematic view of another connector that may mate with the connectors shown in FIGS. 2(B) and 2(C).
Figure 2F:
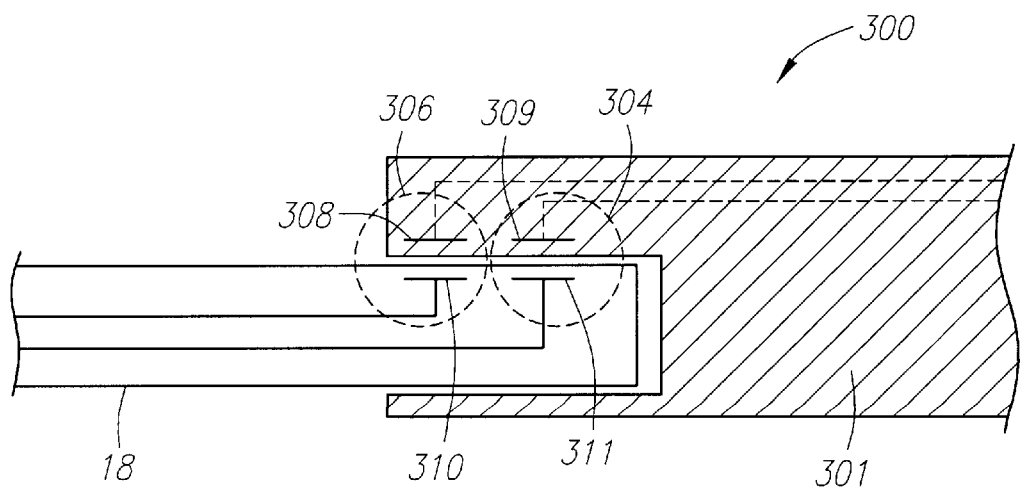
FIG. 2(F) is a circuit schematic illustrating a capacitive coupling in accordance with the present invention.
Figure 2G:
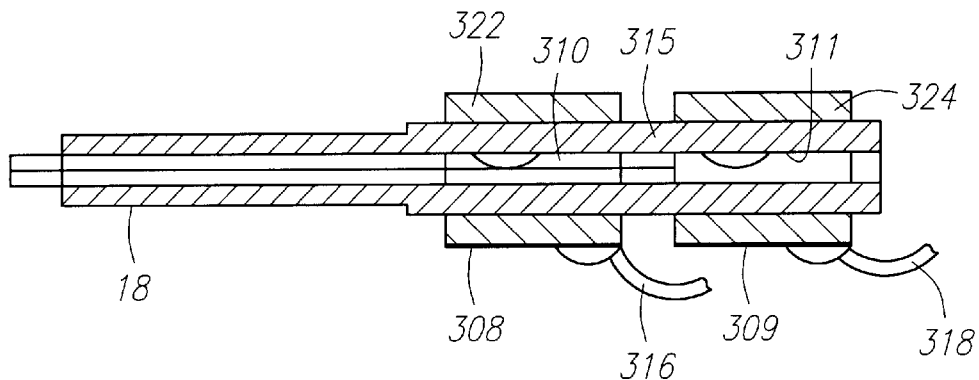
FIG. 2(G) is a cross-sectional view of a portion of a capacitive coupling in accordance with the present invention.

FIG. 2(E) provides an alternative mating connector 174 which is identical to the mating 164 except that the cone tipped spring contact 166 is replaced with a rolled split pin contact 176. The split pin contact 176 has the advantage that it can compress inward as it contacts the inner diameter of the connectors 156 and 170 when the connectors are mated. Again, the slip contact 168 may be substituted with a multi-contact socket connector (not shown).

Turning now to FIGS. 2(F)–2(P), it will be noted that it is not necessary for a physical connection to be made between the leads of the imaging core 18 and those, for example, of the adapter 150. Rather, in accordance with one aspect of the present invention a capacitive coupling or an inductive coupling may be provided between the leads of the imaging core 18 and the circuitry of the adapter 150.

Figure 2H:
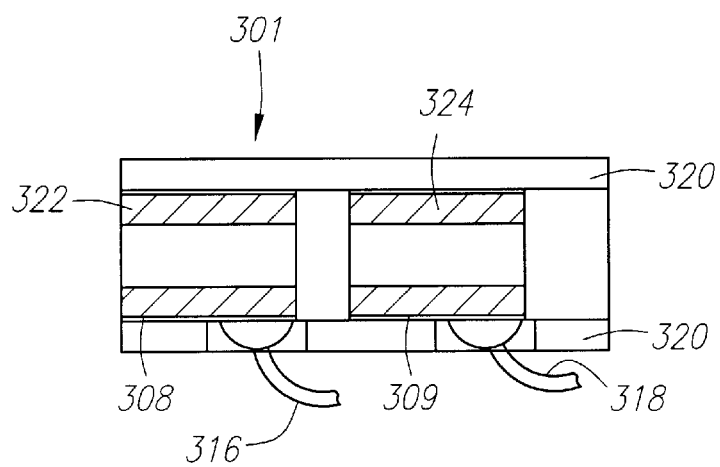
FIG. 2(H) is an enlarged cross-sectional view of a female portion of the capacitive coupling shown in FIG. 2(G).
Figure 2I:
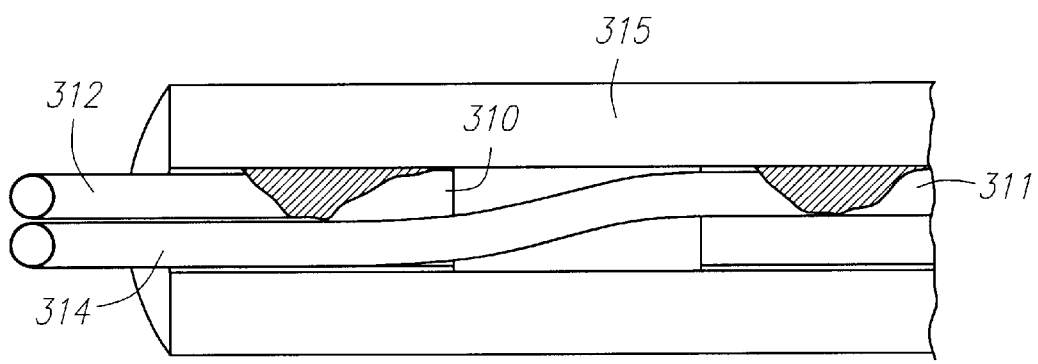
FIG. 2(I) is an enlarged cross-sectional view of a male portion of the capacitive coupling shown in FIG. 2(G).
Figure 2J:
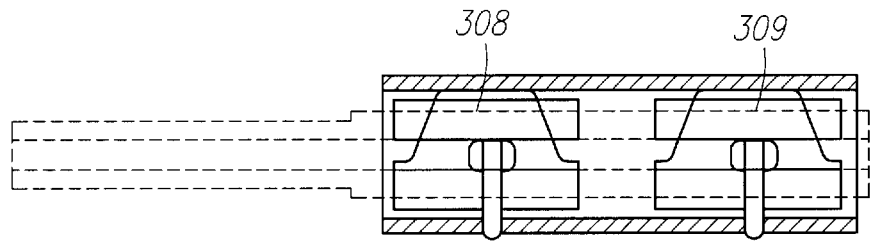
FIG. 2(J) is an illustration of a preferred type of electrode contact that may be used within a capacitive coupling in accordance with the present invention.
Figure 2K:
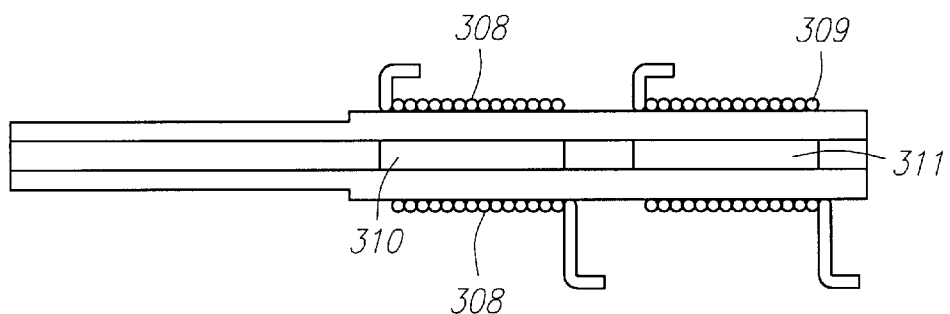
FIG. 2(K) is an illustration of another preferred type of electrode contact that may be used within a capacitive coupling in accordance with the present invention.
Figure 2L:
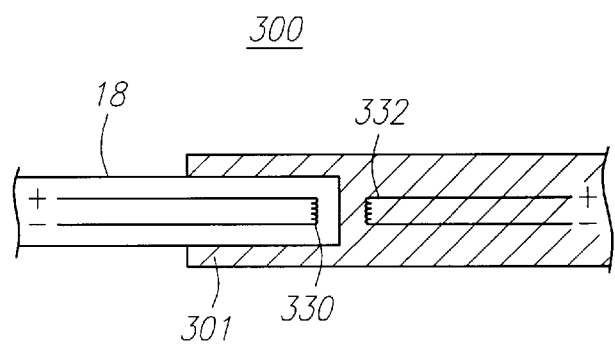
FIG. 2(L) is an electrical schematic of an inductive coupling that may be used in accordance with the present invention.
Figure 2M:
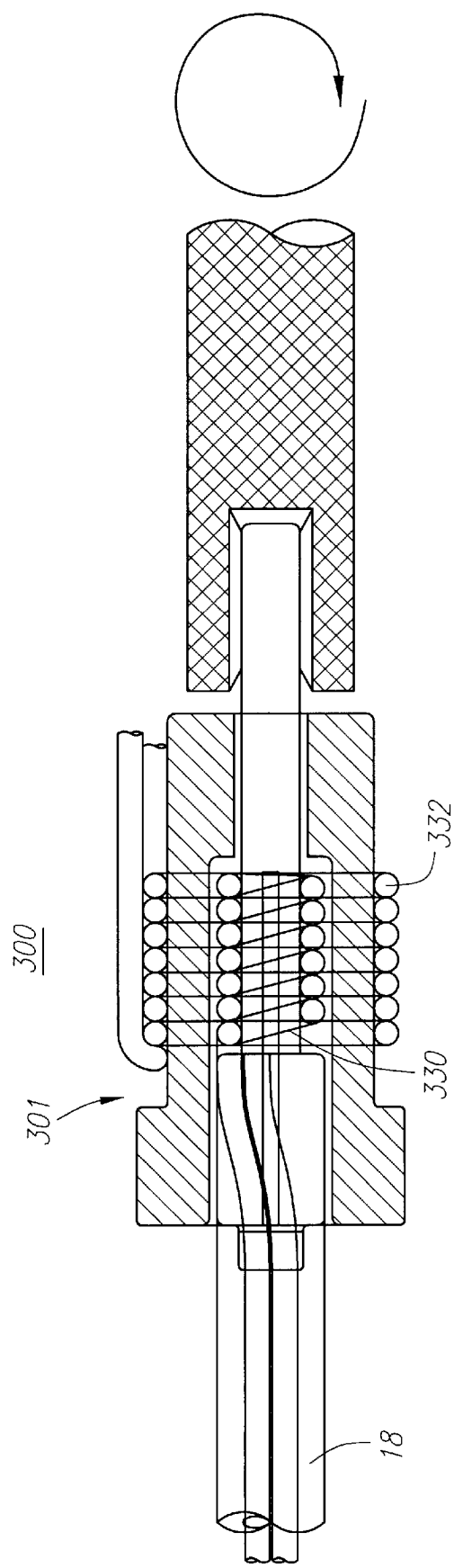
FIG. 2(M) is an illustration of the inductive coupling shown in FIG. 2(L).
Figure 2N:
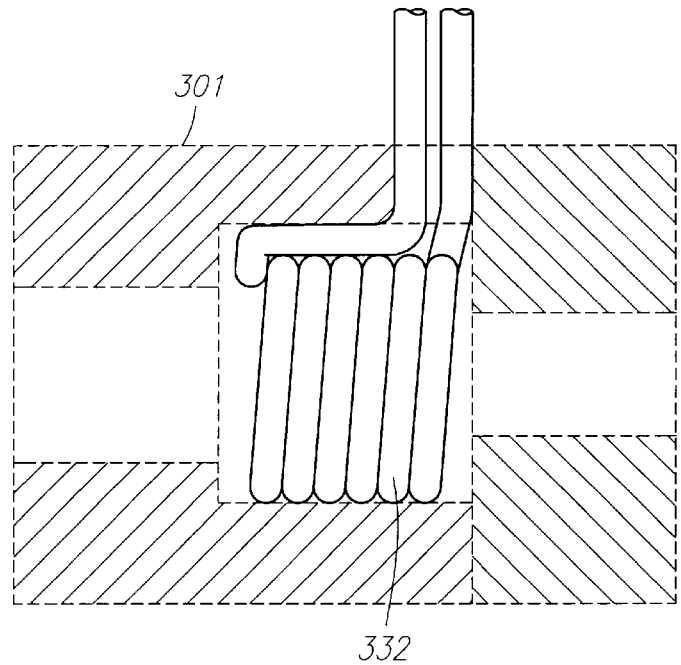
FIG. 2(N) is an illustration of a female portion of the inductive coupling shown in FIG. 2(M).
Figure 2O:
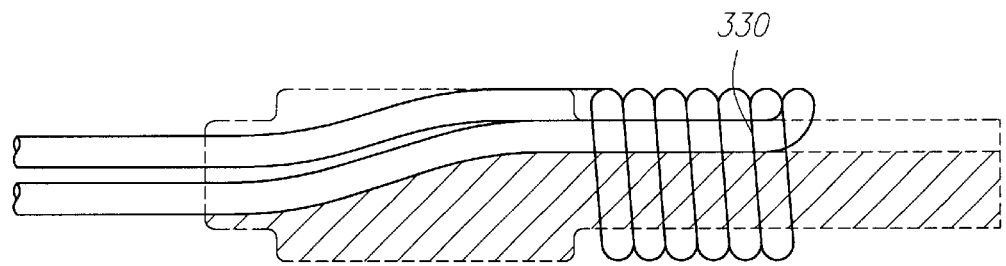
FIG. 2(O) is an illustration of a male portion of the inductive coupling shown in FIG. 2(M).

For example, as is shown in FIGS. 2(F)–2(K), in one embodiment a mating connector 300 may take the form of a capacitive coupling. In such an embodiment, a pair of capacitors 304 and 306 are formed by respective electrode plates 308–311 formed within the proximal end of the imaging core 18 and a female receptor 301. As shown in FIG. 2(I), which illustrates the male, guidewire portion of the connector 300, a positive lead 312 and a negative lead 314, which extend from the imaging transducer 56, may be coupled, via soldering or bonding, to the cylindrical electrode plates 310 and 311 formed within the proximal end of the imaging core 18. The cylindrical electrode plates 310 and 311 preferably are encased within a ceramic, dielectric material 315. Further, as shown in FIG. 2(H), the female portion 301 of the connector 300 preferably comprises a pair of cylindrical electrode plates 308 and 309, a pair of positive and negative leads 316 and 318 coupled respectively to the electrode plates 308 and 309, a drive sleeve 320, and a pair of conductive elastomeric sleeves 322 and 324 that are bonded to an inner surface of the electrode plates 308 and 309. It will be noted that the conductive elastomeric sleeves 322 and 324 are provided to ensure intimate contact between the male and female portions of the connector 300, and to ensure that very little, if any, air is allowed to reside in the gaps between the electrode plates 308–311 that form the capacitors 304 and 306. Finally, as is shown in FIGS. 2(J) and 2(K), the electrode plates 308 and 309 provided within the female portion 301 of the connector 300 may take the form of spring members that allow the female portion 301 of the connector 300 to more securely engage the male portion.

Turning now to FIGS. 2(L)–2(O), in still a further alternative embodiment, the connector 300 may take the form of an inductive or transformer type coupling. In such an embodiment, a first coil 330 may be provided within proximal end of the imaging core 18 of the guidewire 10, i.e., within the male portion of the connector 300, and a second coil 332 may be provided within the female portion 301 of the connector 300. Those skilled in the art will appreciate that the locations of the coils 330 and 332 may vary from those illustrated in FIGS. 2(M)–2(O) without altering to any significant degree the basic structure and operation of the connector 300. For example, the coil 332 of the female portion of the connector 300 may be configured to engage an exterior surface of the male portion of the connector, or the coil 332 may be located, for example, within or around an exterior surface of the female portion 301 of the connector 300. It also will be appreciated that, with respect to the embodiment of the connector shown in FIGS. 2(L)–2(O), it is possible, if desired, for the male and female portions of the connector 300 to rotate as a single unit, possible for the male and female portions of the connector 300 to rotate independently of one another, and possible for only the male portion of the connector to be rotatable within the adapter 150.

In view of the foregoing, those skilled in the art will appreciate that any of the above described connectors may be used with an imaging guidewire in accordance with the present invention and, moreover, that portions of the above-described connectors might be combined to provide still additional coupling methodologies. For example, a connector might comprise a physical connection or contact, as described with reference to FIGS. 2(A)–2(E) above, and a capacitive contact or coupling, as described with reference to FIGS. 2(F)–2(K) above.

Turning again to FIGS. 1, 1(A)–1(C), 2 and 3, the imaging core 18 is slidably and rotatably received within the guidewire body 16 such that the imaging core 18 may be axially translated relative to the guidewire. In this way, the imaging device 42 can be axially translated along the imaging portion 26 of the guidewire body 16 thereby enabling imaging along an axial length of a region of tissue without moving the guidewire body 16. Hence, the proper positioning of the guidewire 10 within the patient's body is maintained so that it may effectively serve as a guidewire for the insertion of catheters.

Prior to inserting the imaging guidewire 10 into a vessel in a body, the imaging guidewire 10 may be filled or flushed with fluid, for example water, to expel air. Residual air in the imaging guidewire 10 can impair imaging especially if using an ultrasound imaging system. The flush may be accomplished by any suitable method such as the Tuohy Borst (aspiration through two valves), providing an open distal (body pressure maintains flush), or simply filling through the proximal end of the imaging guidewire 10.

Figure 4:
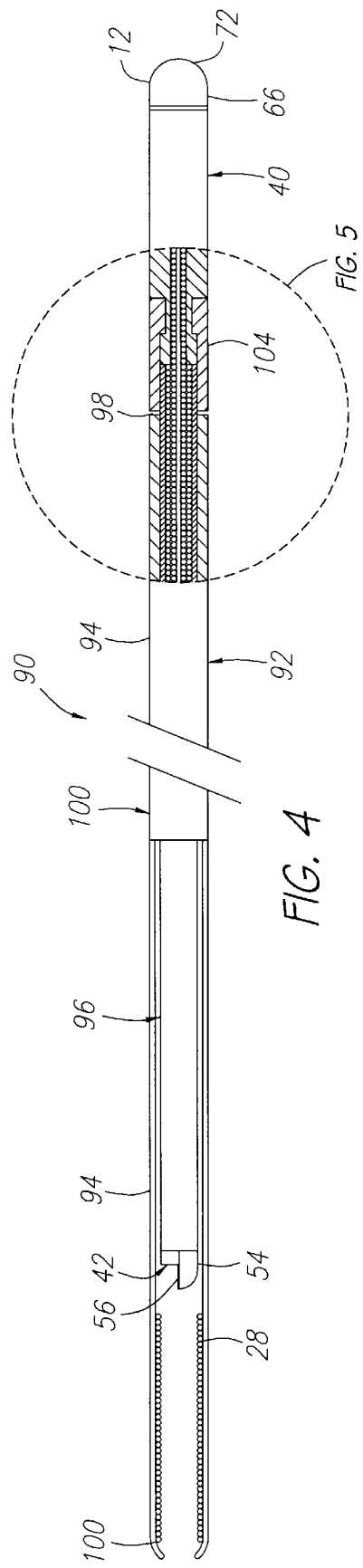
FIG. 4 is a partial cross-sectional view of an alternative imaging guidewire in accordance with the present invention.
Figure 5:
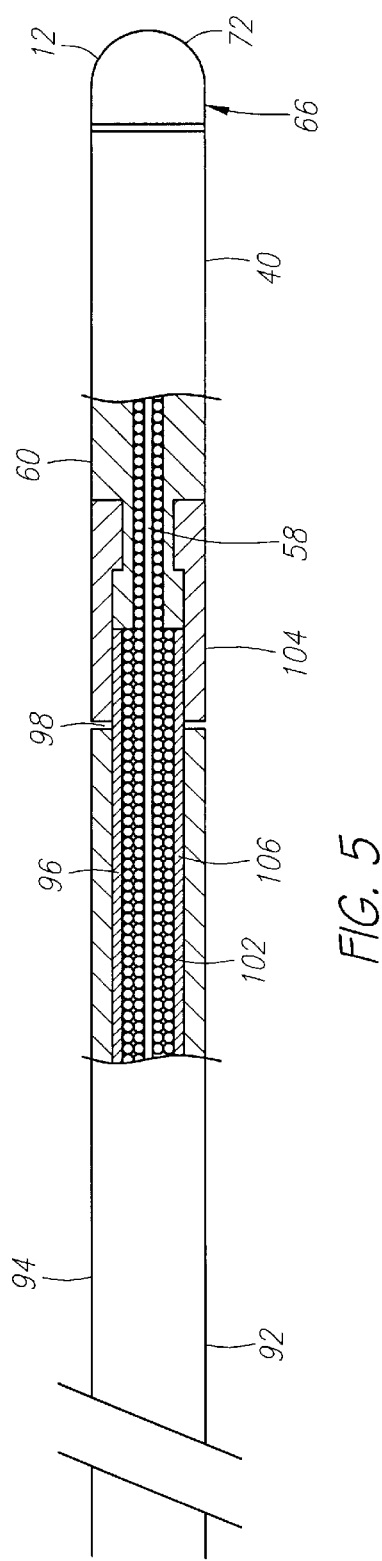
FIG. 5 is an expanded cross-sectional view of the region as designated in FIG. 4.

An alternative embodiment of an imaging guidewire 90 is shown in FIGS. 4–5. The imaging guidewire 90 is similar to, and includes many of the features and elements as, the imaging guidewire 10 described above. Throughout the description and figures, like reference numerals refer to like elements and therefore, some elements are not explicitly described for all figures.

The main differences of the imaging guidewire 90 are the use of a single polymer sheath 94 for the guidewire body 92, and a modified imaging core 96. The guidewire body 92 is formed of a single piece polymer sheath 94 having a proximal end 98 and a distal end 100. Preferred polymer sheath materials include polyimide and PEEK. The sheath 94 extends from the connector 40 to the imaging portion 26 of the guidewire 90. A nonrotating union collar 104 may be inserted between the rotatable connector 40 and the nonrotating sheath 94 to provide rotation on the internal core and allow non-rotation of the stiffening sleeve (telescope) 106.

The imaging core 96 comprises a drive cable 102 having the imaging device 42 attached to its distal end and the connector 40 attached to its proximal end. The drive cable 102 is preferably a counter-wound, multi-filar coil as described above. A stiffening sleeve 106 preferably formed of a flexible tube such as a NITINOL tube, is disposed between the drive cable 102 and the sheath 94. The polymer sheath 94 may not provide sufficient rigidity and pushability to the guidewire and therefore, the stiffening sleeve 106 gives the guidewire these properties. The stiffening sleeve 106 is received into the union collar 104 and extends distally to the imaging device 42. In an alternative form, the stiffening sleeve 106 could extend distally to a predetermined distance short of the imaging device 42, preferably about 15 cm short. The stiffening sleeve 106 preferably does not rotate with the drive cable 102.

The method of using the imaging guidewire 90 is virtually identical to that described above for imaging guidewire 10. However, use of the imaging guidewire 90 may allow for extended telescopic action of the guidewire. In some embodiments, as much as, for example, 150 cm of telescopic extension may be provided.

Figure 6:
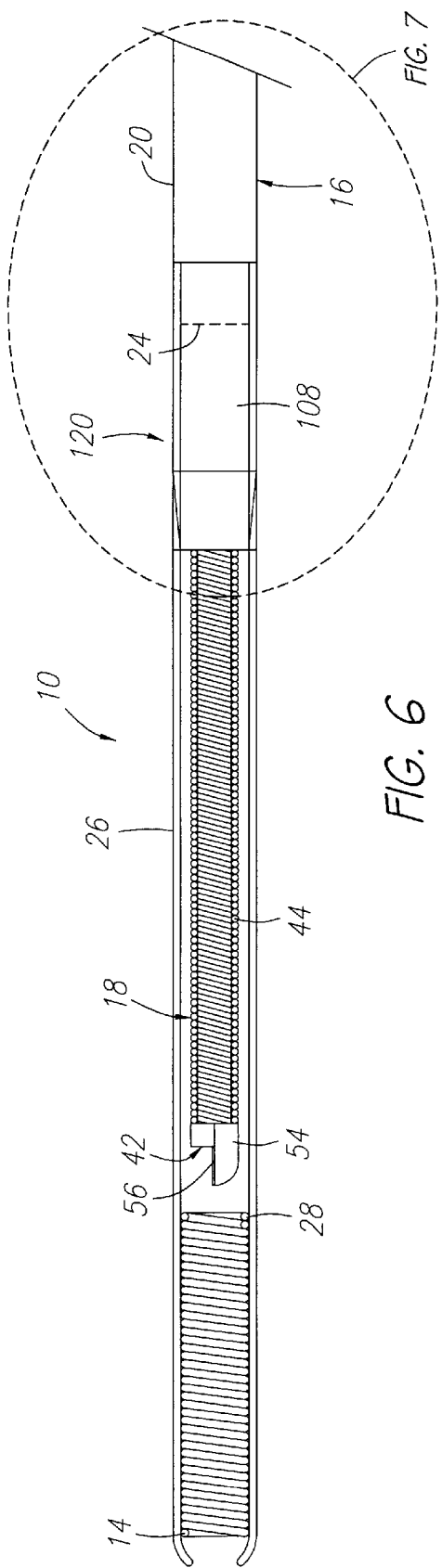
FIG. 6 is a partial cross-sectional view of another alternative imaging guidewire in accordance with the present invention.
Figure 7:
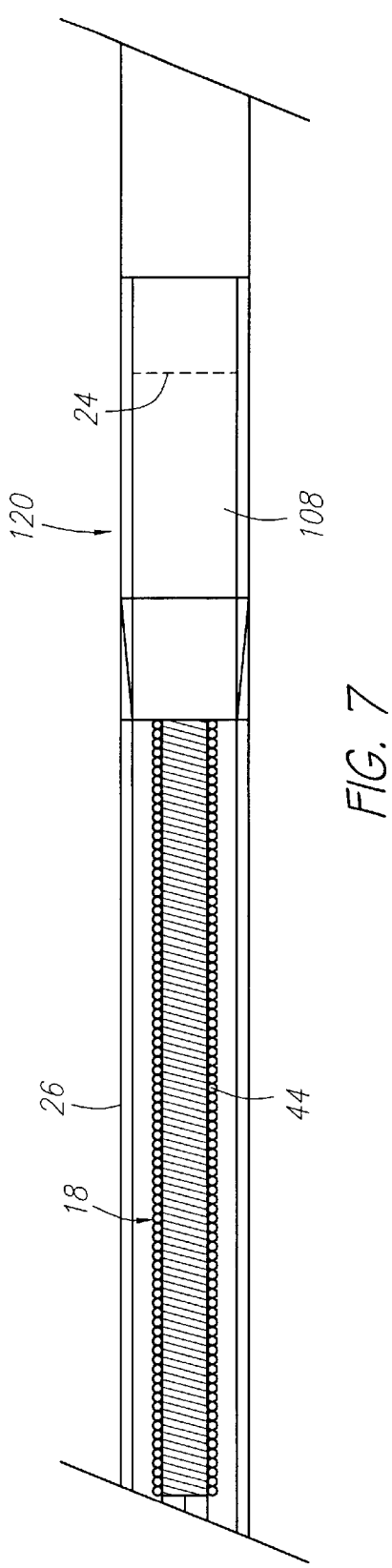
FIG. 7 is an expanded cross-sectional view of the region as designated in FIG. 6.

FIGS. 6–7 show an imaging guidewire 10 having an improvement in the transition from the stiffer main body 20 of the guidewire body 16 to the softer, more pliable imaging portion 26 according to the present invention. A relatively large difference in the stiffness of the main body 20 and the imaging portion 26 can create a stress riser at the connection point which tends to cause the more flexible imaging portion 26 to bend sharply and/or kink when the guidewire is routed through small radius paths. To relieve this condition, instead of bonding the imaging portion 26 directly to the main body 20 as described above, a graduated transition 120 comprising a short transition tube 108 is attached to the distal end 24 of the main body 20 and the imaging portion 26 is attached to the other end of the transition tube 108. The transition tube is made of a material, and is configured, such that it has a stiffness between that of the main body 20 and the imaging portion 26.

Figure 8:
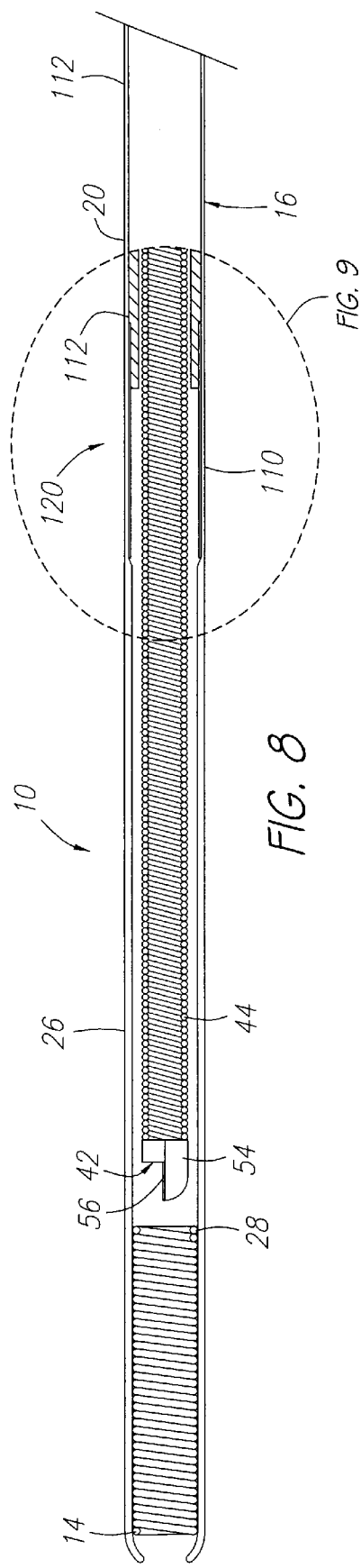
FIG. 8 is a partial cross-sectional view of another alternative imaging guidewire in accordance with the present invention.
Figure 9:
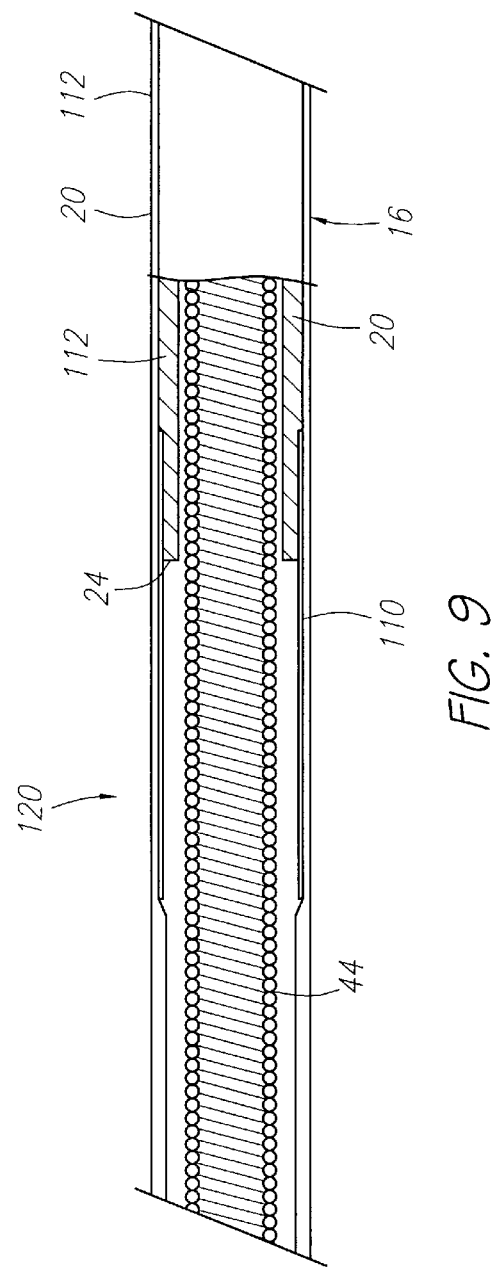
FIG. 9 is an expanded cross-sectional view of the region as designated in FIG. 8.

FIGS. 8–9 show an alternative configuration for the graduated transition 120 between the main body 20 and the imaging portion 26 similar to that described with respect to FIGS. 6–7, except that the distal end of the transition tube 110 is left free. The outer diameter of the main body 20 is reduced from that described above to accommodate a full length jacket 112 comprising a thin layer of plastic, preferably polyethylene, to be formed over the entire length of the main body 20. The preferred reduced thickness of the main body 20 is preferably about 0.032" corresponding to a jacket 110 thickness of about 0.0015". The imaging portion 26 and the jacket 112 may be formed from a single varying thickness piece of material. In this configuration, the transition tube 110 is similar in construction and materials to the transition tube 108 described above.

Another variation of a graduated transition 120 between the main body 20 and the imaging portion 26 is shown in FIGS. 10–11. The imaging guidewire 10 of FIGS. 10–11 is identical to that shown in FIGS. 1–3 except that the distal end 24 of the main body 20 is constructed in a spiral form 114 with increasing pitch as it extends distally. Then, the imaging portion 26 extends over the spiral form 114. The spiral form 114 creates a more flexible portion of the main body 20 that performs the graduated transition function similar the that described above.

FIGS. 12–13 depict yet another embodiment of an imaging guidewire 10 having a graduated transition 120. The imaging guidewire 10 of FIGS. 12–13 is identical to that of FIGS. 10–11 except that the spiral form 114 is replaced with a tapered finger section 116.

Figure 14:
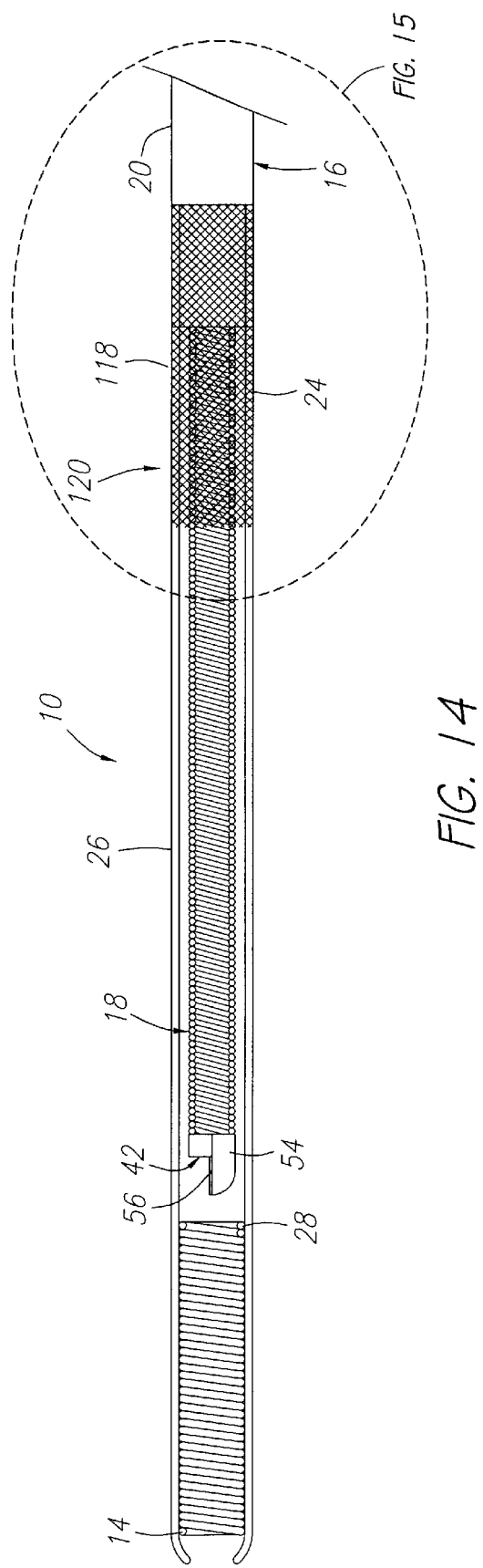
FIG. 14 is a partial cross-sectional view of another alternative imaging guidewire in accordance with the present invention.
Figure 15:
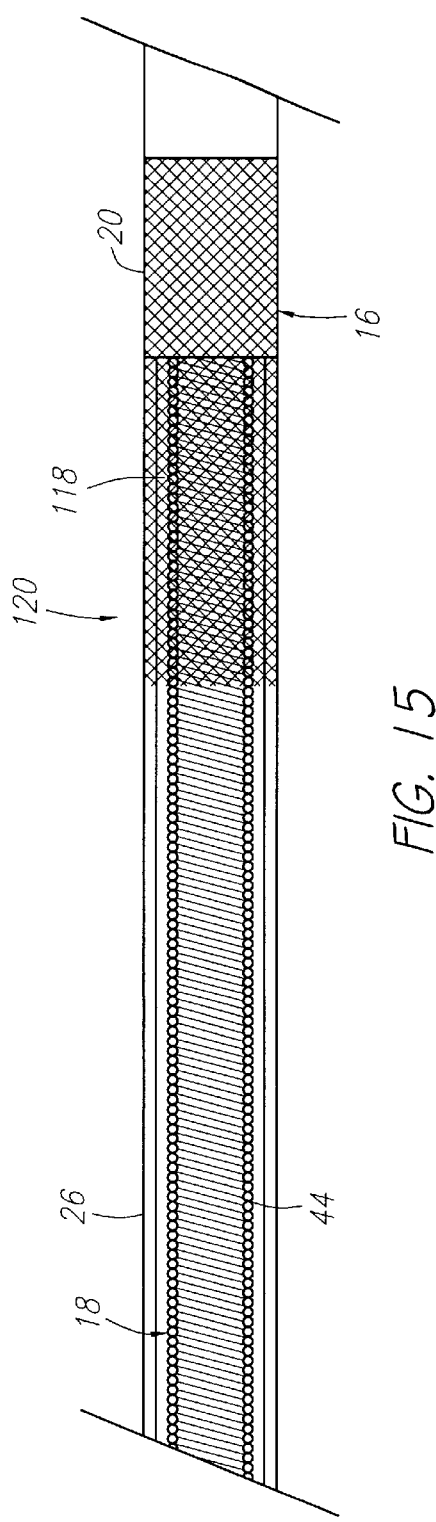
FIG. 15 is an expanded cross-sectional view of the region as designated in FIG. 14.

Still another embodiment of graduated transition 120 on an imaging guidewire 10 is shown in FIGS. 14–15. In this embodiment, a reinforcing braided section 118 is placed over the connection between the imaging portion 26 and the main body 20. The braided section 118 may be made of plastic such as polyethylene, co-extruded polymer materials, or any other suitable material. The braided section 118 performs similarly to the graduated transitions described above.

Except for the varying graduated transition configurations of the guidewire body 16, the imaging guidewires 10 of FIGS. 6–15 are identical to the imaging guidewire described for FIGS. 1–3. In addition, the method of using the imaging guidewires is the same as previously described.

The stress relief transition from the main body 20 to the imaging portion 26 may also be accomplished by varying the cross-sectional thickness of the main body 20 and/or the imaging portion 26 at the interface of the two tubes. Varying the thickness of the tubes in turn changes the stiffness of the tube. For example, the thickness of the main body 20 and/or the imaging portion 26 may be tapered, stepped or angle cut. Hence, if the main body 20 is made of a stiffer tube than the imaging portion 26, the main body 20 would be made gradually thinner as it extends distally toward the imaging portion 26; and/or the imaging portion 26 would be gradually thickened as it extends proximally toward the main body 20. An example of the varying thickness transition using a tapered main body and imaging portion 26 is shown in FIG. 16.

Turning now also to FIGS. 17–20, in one presently preferred form, the imaging guidewire 10 or 90 is capable of disconnectably mating with an adapter 150 which, in turn, couples to a motor drive unit 152, as is shown in FIG. 1. The motor drive unit 152 may comprise, for example, a model MDU-4 motor drive unit currently distributed by Boston Scientific Corp. Thus, the adapter 150 may be coupled in a conventional manner to the motor drive unit 152, and the structure and function of the motor drive unit 152 need not be described in detail herein, as the structure and function of the model MDU-4 motor drive unit is believed to be well known in the art. Nonetheless, it should be appreciated that a principal function of the adapter 150 and motor drive unit 152 is to provide a conduit for transmitting an imaging signal from the imaging guidewire 10 or 90 to the signal processing equipment 154. In addition, the motor drive unit 152 and adapter 150 preferably are configured to provide a mechanical coupling to the imaging guidewire 10 or 90 such that torque may be applied by a motor (not shown) within the motor drive unit 152 via the adapter 150 to the drive cable 50 of the imaging guidewire 10 or 90. Finally, those skilled in the art will also appreciate that the motor drive unit 152 and adapter 150 may be formed, if desired, as a single unit.

Turning now in particular to FIG. 17, the motor drive unit 152 may comprise a model MDU-4 motor drive unit manufactured and distributed by Boston Scientific Corp. and preferably includes a case 186 which provides a port 187 for coupling to the adapter 150. The port 187 provides both a mechanical and an electrical interface between the motor drive unit 152 and the adapter 150. The motor drive unit 152 and adapter 150 also include various electronic circuits (not shown) for transmitting an imaging signal from the imaging guidewire 10 and 90 to the signal processing equipment 154. The electronics within the motor drive unit 152 are connected to an electrical cable 190 that extends out of the case 186 of the motor drive unit 152 and is connectable to the signal processing electronics 154 (see FIG. 1) by a connector (not shown).

While in the currently preferred embodiment a motor (not shown) is provided within the motor drive unit 152, it will be appreciated that in alternative embodiments a motor for rotating the imaging core 18 may be external to the drive unit 152 and may be a part, for example, of the signal processing equipment 154. In such embodiments, a motor drive cable may extend out of the case 186 of the motor drive unit 152 and have a connector that is connectable to the motor (not shown). Within the case 186 of the motor drive unit 152, the motor drive cable would connect to a drive mechanism that, in turn, would transmit rotational torque from the drive cable to a drive mechanism within the adapter 150.

Figure 20:
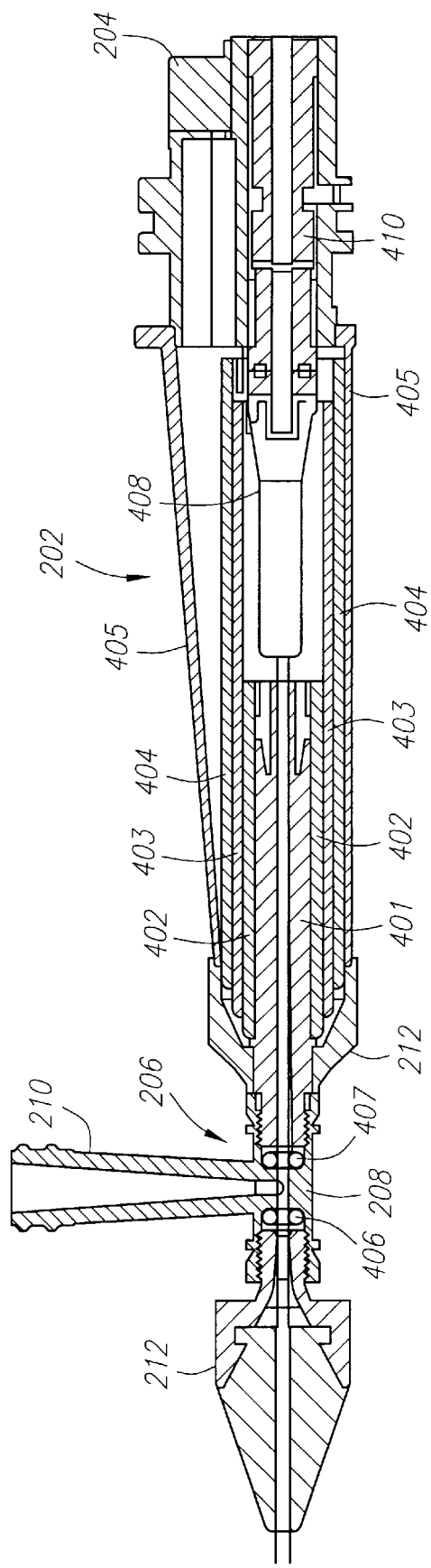
FIG. 20 is a cross-sectional view of the adapter of FIG. 18.

Turning now in particular to FIGS. 18–20, it is presently preferred that the adapter 150 removably plug into the drive unit 152 via the port 187. In an exemplary embodiment, the adapter 150 comprises a telescoping cover 202. The telescoping cover 202 preferably has 2 or more plastic telescoping sections, and 5 telescoping sections 401–405 are shown in FIGS. 19 and 20. An adapter connector 204 is disposed on the proximal end of the adapter 150 and mechanically and electrically connects to a drive unit connector (not shown) provided within port 187 (shown in FIG. 17) of the motor drive unit 152. An adapter flushport 206 is located on the end of the adapter cover 202. In an exemplary embodiment, the flushport 206 is a T-shaped fitting having a main through port 208 and a side port 210. Threaded knobs 212 on either side of the through port 208 are provided to compress o-ring seals 406 disposed therein. When compressed, the o-ring seals 406 and 407 fit tightly against an outer wall of an imaging guidewire 10 or 90 that has been inserted into the adapter 150. The forward o-ring seal 406 may also be compressed against the exterior surface of a catheter (not shown), when the guidewire 10 or 90 is located within a lumen of the catheter. The side port 210 is preferably a luer fitting that allows for typical syringe type coupling to the main through port 208.

The telescoping adapter cover 202 protects the imaging core 18 from being openly exposed during pull-back procedures where the imaging core 18 is translated relative to in the body 16. This is important because eliminating such exposure can prevent the imaging signal from being distorted thereby preserving image quality. Moreover, the telescoping adapter cover 150 can be retracted out of the way during catheter exchanges over the guidewire such that the guidewire can be disconnected and reconnected to the adapter.

Those skilled in the art will appreciate that in alternative embodiments, the adapter 150 may utilize a non-telescoping cover, and that with the exception of lacking a telescoping function, such an adapter would function in virtually the same manner as the adapter 150 shown in FIGS. 18–20.

Turning now to FIG. 20, there is shown a cross-sectional view of the adapter 150 having a proximal end of a guidewire 10 inserted therein. As shown, the proximal end of an imaging core 18 of the guidewire 10 is inserted into a female portion of a connector (not shown) that is disposed within a collet assembly 408. The female portion of the connector provided within the collet assembly 408 preferably is of the type described above with reference to FIGS. 2(A)–2(O) above. Thus, it will be appreciated that the female portion of the connector provided within the collet assembly 408 provides both a mechanical and electrical interface between the imaging core 18 of the guidewire 10 and the drive mechanism 410 and electronics (not shown) of the adapter 150.

Figure 21:
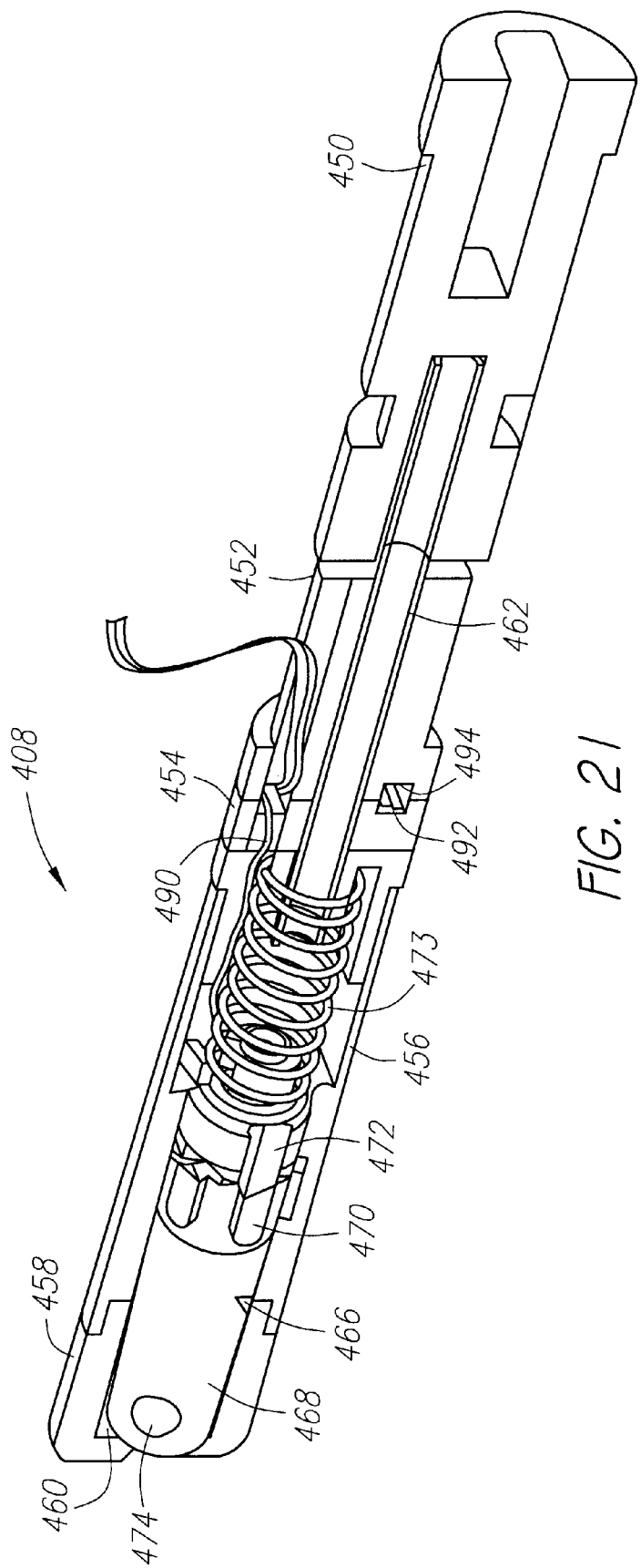
FIG. 21 is a cut-away view of a collet assembly that may be used in an adapter in accordance with the present invention.
Figure 22:
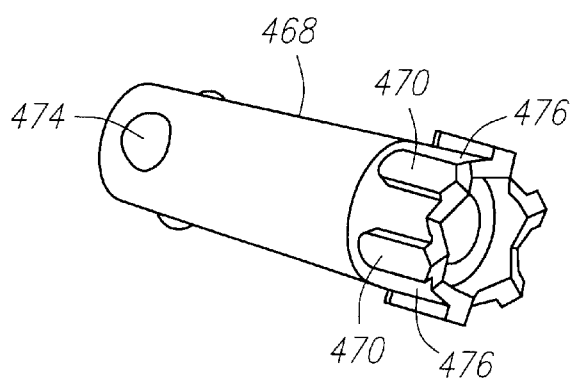
FIG. 22 is a perspective view of contact housing and stationary pawl of the collet assembly shown in FIG. 21.
Figure 23:
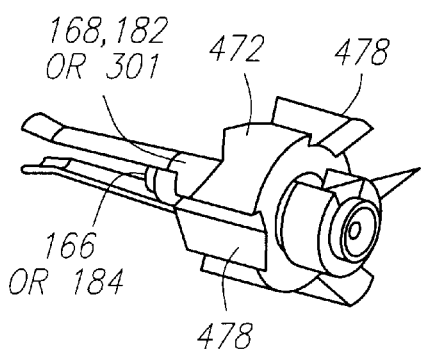
FIG. 23 is a perspective view of a rotary pawl and connector assembly of the collet assembly shown in FIG. 21.
Figure 24:
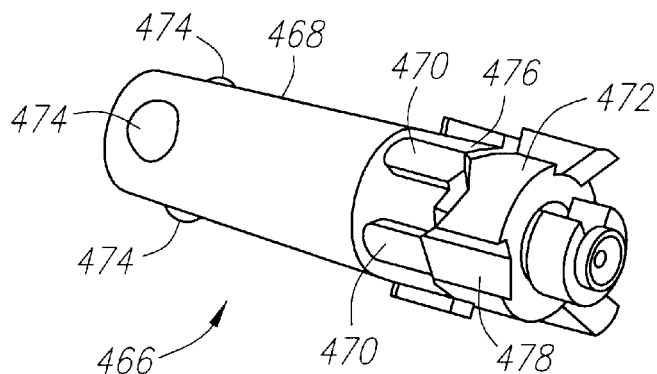
FIG. 24 is an illustration of an imaging core engaging mechanism used within the collet assembly shown in FIG. 21.

Turning now also to FIG. 21, a collet assembly 408 in accordance with the present invention may comprise, for example, a rotator 450 that engages a drive shaft (not shown) of a motor drive unit 152, a fixed ferrite 452, a rotating ferrite 454, a main collet body 456 and a collet cone 458 having a tapered inner cavity 460. The rotator 450 is mechanically coupled to the rotating ferrite 454 by a drive shaft tube 462, and the rotating ferrite 454 is fixedly attached to the main collet body 456. The collet cone 458 is attached to a distal end of the main collet body 456. A tapered cavity 464 is defined within the collet cone 458 and the main collet body 456, and an imaging core engaging mechanism 466 is provided within the tapered cavity 460.

Turning now in addition to FIGS. 22–25, the imaging core engaging mechanism 466 comprises a contact housing 468 that is coupled to a stationary pawl 470, a rotary pawl 472 that has a female portion 168, 182 or 301 of a connector mounted therein, and a spring 473 that engages the rotary pawl 472 and a proximal, internal section of the collet main body 456. In addition, three ball bearings 474 are preferably disposed within respective cavities or recesses 476 formed within a distal end of the contact housing 468.

Figure 25:
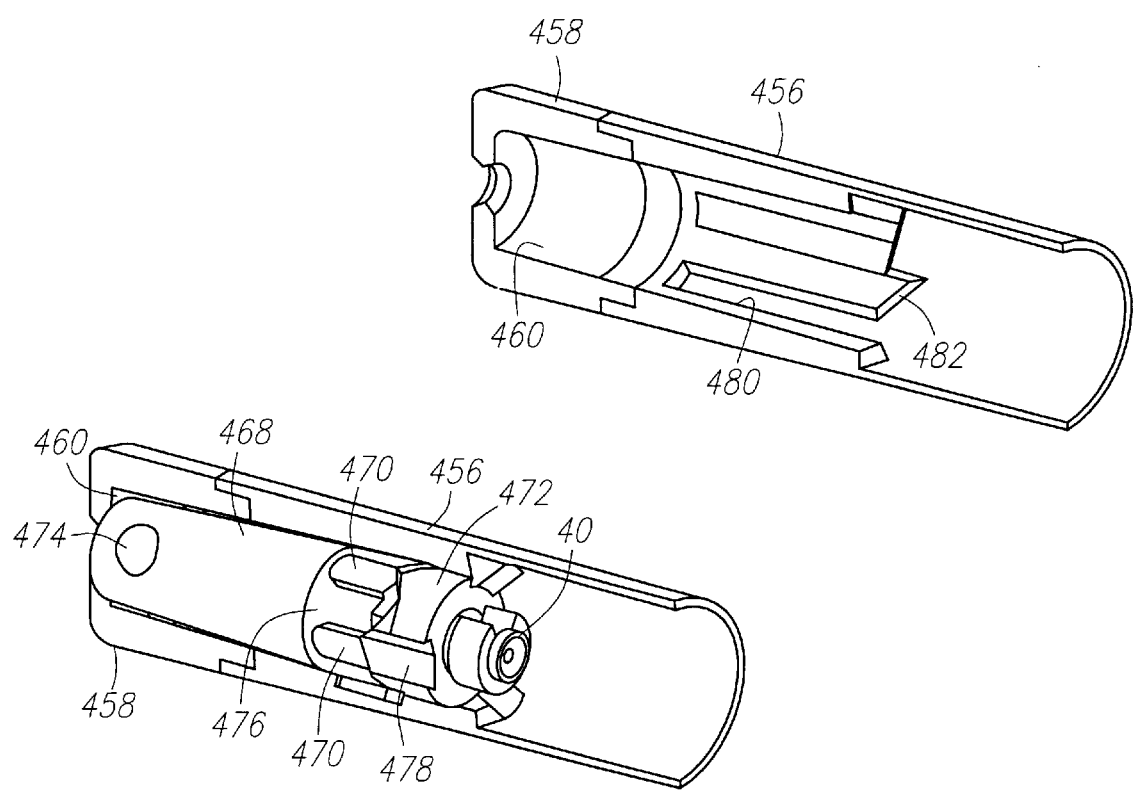
FIG. 25 is a cut-away view of a portion of the collet assembly shown in FIG. 21.

Those skilled in the art will appreciate that the stationary pawl 470, rotary pawl 472 and spring 473 function in a manner quite similar operating mechanism of a conventional ball point pen. Thus, when the collet assembly 408 is assembled and disposed within an adapter 150, the proximal end of an imaging guide wire 10 or 90 may be inserted through an opening in the distal end of the adapter 150 and into the collet assembly 408. As the guidewire 10 or 90 is pushed into the female connector 168, 182 or 301 of the collet assembly 408, the rotary pawl 472 compresses the spring 473 allowing the core engaging mechanism 466 (including the contact housing 468, stationary pawl 470 and rotary pawl 472) to move progressively within the main body 456 of the collet assembly 408 in the direction of the rotator 450. That movement affords the ball bearings 474 housed within the contact housing 468 additional space within the tapered cavity 460. As the imaging core engaging mechanism 466 moves further toward the rotator 450, force is applied by a linear indexing ratchet 476 located on the stationary pawl 470 to a rotary indexing ratchet 478 located on the rotary pawl 472 urging the rotary pawl 472 to rotate about a central axis (not shown) of the collet assembly 408. However, as shown in FIG. 25, the indexing ratchets 476 and 478 travel within channels 480 formed within an inner wall of the collet main body 456, until the rotary indexing ratchet 478 escapes the channel 480. At that time, the rotary indexing ratchet 478 and, thus, the rotating pawl 472 rotate about the central axis of the collet assembly 408. The rotary indexing ratchet 478 then may engage surface 482 adjacent the channel 480. When the guidewire 10 or 90 is pushed into the female connector 168, 182 or 301 of the collet assembly 408 again, the rotary indexing ratchet 478 disengages the surface 482 and is caused to rotate in a manner such that it may pass into the channel 480. As the imaging core engaging mechanism 466 moves toward the cone 458, the ball bearings 474 are driven against the imaging core 18 by the wall of the tapered cavity 460. Thus, it will be appreciated that, once the imaging core 18 is locked within the imaging core engaging mechanism 466, pulling on the imaging core 18 in a direction away from the rotator 450 will only cause the imaging core engaging mechanism 466 to more tightly engage the imaging core 18.

Now, turning back to FIG. 21, imaging signals provided to the female connector 168, 182 or 301 are carried on a pair of wires 490 to a first transformer coil 492. The signals then are transmitted to a second transformer coil 494 by means of inductive coupling and, from there, the signals may be conveyed to the contacts (not shown) provided within the housing of the adapter 150 for transmission to the motor drive unit 152 and eventually to the processing system 154.

In view of the foregoing, the reader will see that the present invention provides an improved imaging guidewire. While the above description contains many specifics, these should not be construed as limitations on the scope of the invention, but rather as examples of particular embodiments thereof. Many other variations are possible.

Accordingly, the scope of the present invention should be determined not by the embodiments illustrated above, but rather, the invention is to cover all modifications, alternatives and legal equivalents falling within the spirit and scope of the appended claims.

What is claimed is:

1. An imaging guidewire comprising:
   a body in the form of an elongate flexible tubular member, said body having a proximal end and a distal end, at least a portion of said body being at least substantially transparent to imaging energy;
   a flexible elongate imaging core slidably received within said body, said imaging core having a shaft and an imaging device mounted on a distal end of said shaft and arranged to position said imaging device in axial relation to said substantially transparent portion of said body, said imaging device adapted to receive imaging energy related to internal body structures and to transmit imaging signals to an imaging signal processor;
   the imaging guidewire having a maximum diameter along its entire length not exceeding that which can effectively receive a guidewire lumen of an intravascular catheter;
   wherein said imaging core is axially translatable relative to said body to enable axial translation of said imaging device; and
   a connector on the proximal end of the shaft adapted to provide only a mechanical connection to a mating connector on a drive unit.

2. The imaging guidewire of claim 1 wherein said maximum diameter of the imaging guidewire is 0.035".

3. The imaging guidewire of claim 2 wherein said imaging core is rotatable within said body, said shaft is a drive shaft for rotating said imaging device and said connector is detachably connectable with a mating connector to engage a drive unit to rotate said drive shaft.

4. The imaging guidewire of claim 3 wherein said imaging device comprises an ultrasound transducer arranged to transmit an receive ultrasonic signals to and from the internal body structure.

5. The imaging guidewire of claim 2 further comprising a connector attached to a proximal end of said shaft, said connector being detachably connectable with a mating connector to operatively connect the imaging device to the imaging signal processor while simultaneously engaging a drive unit to rotate said shaft and wherein said imaging core is rotatable within said body, said shaft is a drive shaft for rotating said imaging device and said connector is detachably connectable with a mating connector to engage a drive unit to rotate said drive shaft.

6. The imaging guidewire of claim 1 further comprising a connector attached to a proximal end of said shaft, said connector being detachably connectable with a mating connector to operatively connect the imaging device to the, imaging signal processor.

7. The imaging guidewire of claim 1 wherein said body comprises a proximal body portion having a proximal end extending from the proximal end of said body and a distal end attached to said substantially transparent portion of said body.

8. The imaging guidewire of claim 7 further comprising a stiffening tube disposed between said body and said shaft, said stiffening tube extending from said proximal end of the guidewire to the proximal end of said transparent portion of said body.

9. The imaging guidewire of claim 7 wherein said proximal body portion is formed of a NITINOL tube.

10. The imaging guidewire of claim 9 wherein said shaft comprises a proximal telescope portion having a distal end connected to a drive cable formed of counter-wound, multifilar coils.

11. The imaging guidewire of claim 7 further comprising a transition means between said proximal body portion and said substantially transparent portion of said body.

12. The image guidewire of claim 11 wherein said transition means comprises a transition tube having a bending stiffness between that of the proximal body portion and the substantially transparent portion of said body.

13. The imaging guidewire of claim 12 wherein further comprising a plastic jacket covering substantially the entire length of said body.

14. The image guidewire of claim 11 wherein said transition means is formed by constructing a distal portion of said proximal body portion in a spiral form, said spiral form having increasing pitch as it extends distally.

15. The image guidewire of claim 11 wherein said transition means is formed by constructing a distal portion of said proximal body portion in tapered finger shape.

16. The imaging guidewire of claim 7 wherein said shaft comprises a proximal telescope portion having a distal end connected to a drive cable formed of counter-wound, multifilar coils.

17. The imaging guidewire of claim 1 wherein said shaft comprises a proximal telescope portion having a distal end connected to a drive cable formed of counter-wound, multifilar coils.

18. An imaging guidewire comprising
   a body in the form of an elongate flexible tubular member, said body having a proximal end and a distal end, at least a portion of said body being at least substantially transparent to imaging energy;
   a flexible elongate imaging core slidably received within said body, said imaging core having a shaft and an imaging device mounted on a distal end of said shaft and arranged to position said imaging device in axial relation to said substantially transparent portion of said body, said imaging device adapted to receive imaging energy related to internal body structures and to transmit imaging signals to an imaging signal processor; and a connector having a distal component including a conductive ring through which a coaxial cable having an inner lead and an outer lead separated by a first insulator is inserted and said conductive ring filled with a first portion of conductive epoxy to electrically connect the outer lead to the conductive ring;

the connector also having a proximal component including a second conductor having stepped tubular section and a ball-shaped end having a cavity, an insulator covering said stepped tubular section, the inner lead and insulation extending through said tubular section and into said cavity, and said cavity filled with a second portion of conductive epoxy to electrically connect said inner lead to said second conductor, said proximal component inserted into said conductive ring by inserting said stepped tubular section covered with said insulator into said conductive ring.

19. A method for diagnosis and treatment of an internal body structure comprising the steps of:

providing an imaging guidewire including;

a body in the form of an elongate flexible tubular member, said body having a proximal end and a distal end, at least a portion of said body being at least substantially transparent to imaging energy;

a flexible elongate imaging core slidably received within said body, said imaging core having a shaft and an imaging device mounted on a distal end of said shaft and arranged to position said imaging device in axial relation to said substantially transparent portion of said body, said imaging device adapted to receive imaging energy related to internal body structures and to transmit imaging signals to an imaging signal processor;

the imaging guidewire having a maximum diameter along its entire length not exceeding that which can effectively receive a guidewire lumen of an intravascular catheter;

wherein said imaging core is axially translatable relative to said body to enable axial translation of said imaging device;

providing, a connector attached to a proximal end of said shaft, said connector providing only a mechanical connection with a mating connect or of a drive unit;

introducing said imaging guidewire into a vessel of a vascular system and routing said imaging guidewire to the internal body structure;

producing images of said internal body structure using said imaging device; and axially translating said imaging core relative to said body to image a length of the internal body structure.

20. The method of claim 19 further comprising the step of routing a catheter having a guidewire lumen over the imaging guidewire and advancing the catheter to the internal body structure.

* * * * *

UNITED STATES PATENT AND TRADEMARK OFFICE
CERTIFICATE OF CORRECTION

PATENT NO.    : 6,261,246 B1
DATED         : July 17, 2001
INVENTOR(S)   : Pantages et al.

It is certified that error appears in the above-identified patent and that said Letters Patent is hereby corrected as shown below:

Column 10,
Line 62, change "0.035'" to -- 0.035" --.

Column 15,
Line 33, change "2" to -- 2 --.
Line 34, change "5" to -- 5 --.

Signed and Sealed this

Tenth Day of September, 2002

Attest:

Attesting Officer

JAMES E. ROGAN
Director of the United States Patent and Trademark Office